US012104150B2

(12) United States Patent
Peng et al.

(10) Patent No.: US 12,104,150 B2
(45) Date of Patent: Oct. 1, 2024

(54) NEAR-INFRARED PHOTOTHERMALLY ACTIVATED CRISPR/CAS9 GENOME EDITING MACHINE

(71) Applicant: The Governors of the University of Alberta, Edmonton (CA)

(72) Inventors: Hanyong Peng, Edmonton (CA); Hongquan Zhang, Ottawa (CA); Xing-Fang Li, Edmonton (CA); Xiaochun Le, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 468 days.

(21) Appl. No.: 17/020,676

(22) Filed: Sep. 14, 2020

(65) Prior Publication Data

US 2021/0079373 A1    Mar. 18, 2021

Related U.S. Application Data

(60) Provisional application No. 62/899,927, filed on Sep. 13, 2019.

(51) Int. Cl.
*C12N 15/10*    (2006.01)
*C12N 9/22*    (2006.01)
*C12N 13/00*    (2006.01)
*C12N 15/113*    (2010.01)

(52) U.S. Cl.
CPC .............. *C12N 15/102* (2013.01); *C12N 9/22* (2013.01); *C12N 13/00* (2013.01); *C12N 15/113* (2013.01); *C12N 2310/3519* (2013.01)

(58) Field of Classification Search
CPC ........ C12N 15/102; C12N 9/22; C12N 13/00; C12N 15/113; C12N 2310/3519; C12N 2310/20
See application file for complete search history.

(56) References Cited

U.S. PATENT DOCUMENTS

2009/0196937 A1* 8/2009 Tae .................. A61K 47/34
                                                 424/501
2017/0283831 A1* 10/2017 Zhang ................ C12N 9/22

OTHER PUBLICATIONS

Young Je Lee, Tae Seok Moon, Design rules of synthetic non-coding RNAs in bacteria, Methods, vol. 143, 2018, pp. 58-69, ISSN 1046-2023 (Year: 2018).*
Houshang Nemati et al., Using siRNA-based spherical nucleic acid nanoparticle conjugates for gene regulation in psoriasis, Journal of Controlled Release, vol. 268, 2017, pp. 259-268, ISSN 0168-3659 (Year: 2017).*
Do, Hai Doan, et al. "Advances on non-invasive physically triggered nucleic acid delivery from nanocarriers." Advanced drug delivery reviews 138 (Jan. 1, 2019): 3-17 (Year: 2019).*
Du et al., "DNA-Nanostructure-Gold-Nanorod Hybrids for Enhanced In Vivo Optoacoustic Imaging and Photothermal Therapy," Adv Mater. 28(45):10000-7 (2016).
Wang et al., "Near-Infrared Photothermally Activated DNAzyme-Gold Nanoshells for Imaging Metal Ions in Living Cells," Angew Chem Int Ed Engl. 56(24):6798-802 (2017).
Wang et al., "Protein Activity Regulation: Inhibition by Closed-Loop Aptamer-Based Structures and Restoration by Near-IR Stimulation," J Am Chemical Soc. 137(33):10576-84 (2015).

* cited by examiner

*Primary Examiner* — Nancy J Leith
*Assistant Examiner* — Kyle T Rega
(74) *Attorney, Agent, or Firm* — Clark & Elbing LLP

(57) ABSTRACT

The present disclosure relates generally to a near-infrared photothermally activated CRISPR/CAS9 genome editing machine.

16 Claims, 31 Drawing Sheets
Specification includes a Sequence Listing.

FIG. 7A

```
                         GUUUUAG A   GCUA G A
GGCAUCGACUUCAAGGAGGA     UAAAAUU G G CGAU   A
                         A       G A  A    A
                          A
                          A
                           GGC U
                           CC   A
                           G  UG
                           U
                           U
                           U
                           A
                           U
                            CA       G
                              ACUU    A
                              UGAA  A A
                                  A
                              GGCACCG A
                            U UCGUGGC  G
                            U U       U
```

SEQ ID NO: 18

FIG. 7B

```
                T16
          ┌──────────────┐                            T CG
HS-TTT GGAACTT CCGTAGCT GAAGTTCG          CCTTGAAG      A
       └──────┘                    HS-TTT GGAACTTC      T
         S8   SEQ ID NO: 17                        C G
                                                 SEQ ID NO: 17
```

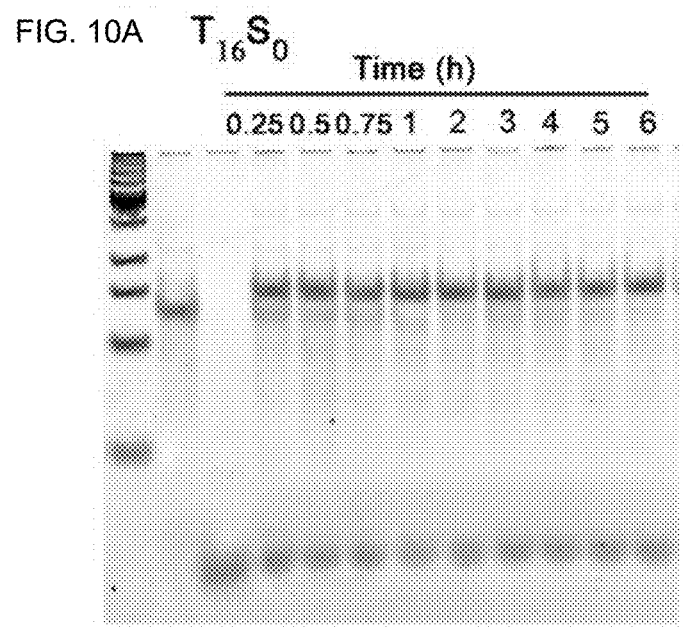
FIG. 10A $T_{16}S_0$
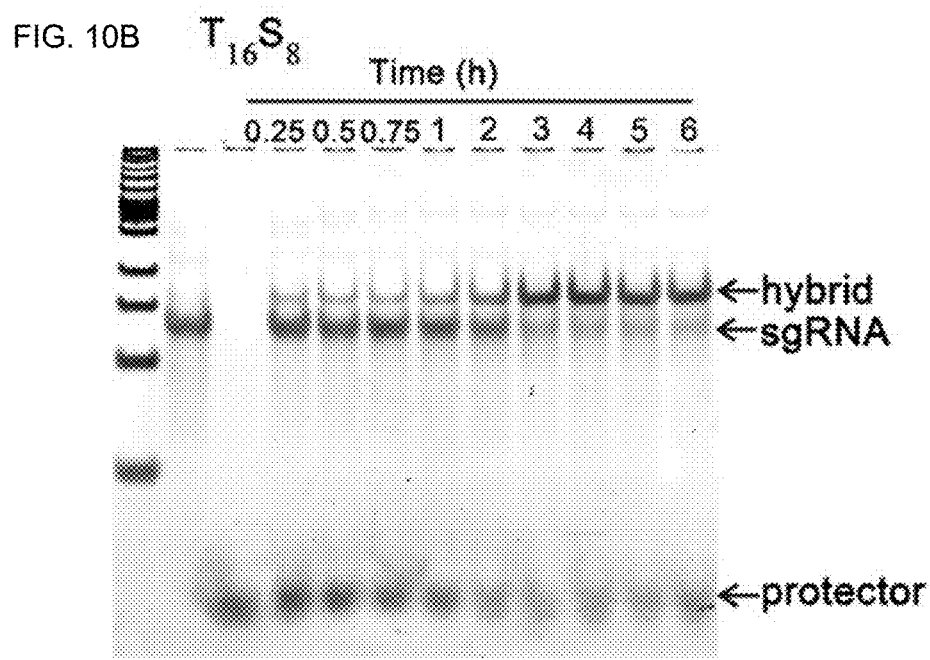
FIG. 10B $T_{16}S_8$

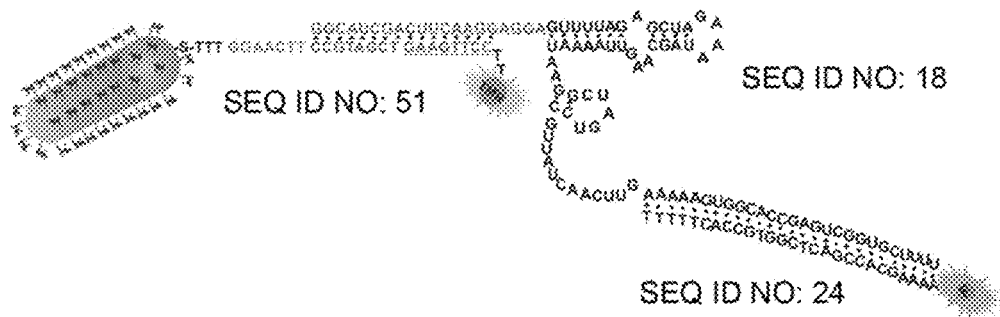
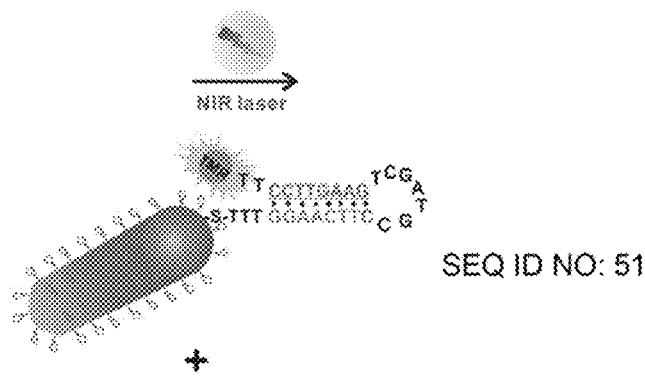
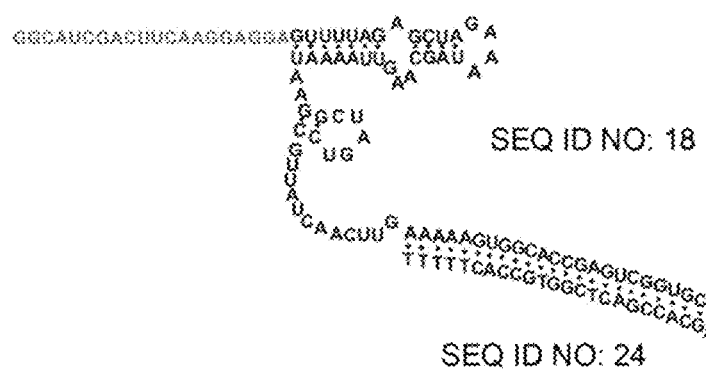
FIG. 28A

SEQUENCE LISTING

<160> NUMBER OF SEQ ID NOS: 52

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
gagtccgagc agaagaagaa ggg                                           23

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gaggccgagc agaagaaaga cgg                                           23

<210> SEQ ID NO 3
<211> LENGTH: 23
<212> TYPE: DNA
<213> ORGANISM: Artificial Sequence

```
<220> FEATURE:
<223> OTHER INFORMATION: primer

<400> SEQUENCE: 3
gagtcctagc aggagaagaa gag                                              23

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gagtctaagc agaagaagaa gag                                              23

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gagttagagc agaagaagaa agg                                              23

<210> SEQ ID NO 6
<211> LENGTH: 13
<212> TYPE: DNA
<213> ORGANISM: Artificial Sequence
<220> FEATURE:
<223> OTHER INFORMATION: primer

<400> SEQUENCE: 6
tgaagtcgat gcc                                                         13

<210> SEQ ID NO 7
<211> LENGTH: 14
<212> TYPE: DNA
<213> ORGANISM: Artificial Sequence
<220> FEATURE:
<223> OTHER INFORMATION: primer

<400> SEQUENCE: 7
ttgaagtcga tgcc                                                        14

<210> SEQ ID NO 8
<211> LENGTH: 15
<212> TYPE: DNA
<213> ORGANISM: Artificial Sequence
<220> FEATURE:
<223> OTHER INFORMATION: primer

<400> SEQUENCE: 8
cttgaagtcg atgcc                                                       15

<210> SEQ ID NO 9
<211> LENGTH: 16
<212> TYPE: DNA
<213> ORGANISM: Artificial Sequence
<220> FEATURE:
<223> OTHER INFORMATION: primer

<400> SEQUENCE: 9
ccttgaagtc gatgcc                                                      16
```

```
<210> SEQ ID NO 10
<211> LENGTH: 17
<212> TYPE: DNA
<213> ORGANISM: Artificial Sequence
<220> FEATURE:
<223> OTHER INFORMATION: primer

<400> SEQUENCE: 10
tccttgaagt cgatgcc                                                   17

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ctccttgaag tcgatgcc                                                  18

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ccttgaagtc gatgcctcaa gg                                             22

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ccttgaagtc gatgccttca ag                                             22

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
ccttgaagtc gatgccttca agg                                            23

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ccttgaagtc gatgccactt caagg                                          25

<210> SEQ ID NO 16
<211> LENGTH: 26
<212> TYPE: DNA
<213> ORGANISM: Artificial Sequence
<220> FEATURE:
<223> OTHER INFORMATION: primer
```

-continued

```
<220> FEATURE:
<221> NAME/KEY: SH
<222> LOCATION: (26)..(26)

<400> SEQUENCE: 16
ccttgaagtc gatgccttt tttttt                                    26

<210> SEQ ID NO 17
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: SH
<222> LOCATION: (26)..(26)

<400> SEQUENCE: 17
ccttgaagtc gatgccttca aggttt                                   26

<210> SEQ ID NO 18
<211> LENGTH: 100
<212> TYPE: RNA
<213> ORGANISM: Artificial Sequence
<220> FEATURE:
<223> OTHER INFORMATION: primer

<400> SEQUENCE: 18
ggcaucgacu ucaaggagga guuuuagagc uagaaauagc aaguuaaaau aaggcuaguc    60
cguuaucaac uugaaaaagu ggcaccgagu cggugcuuuu                         100

<210> SEQ ID NO 19
<211> LENGTH: 100
<212> TYPE: RNA
<213> ORGANISM: Artificial Sequence
<220> FEATURE:
<223> OTHER INFORMATION: primer

<400> SEQUENCE: 19
ggcaucgacu ucaaggaaaa guuuuagagc uagaaauagc aaguuaaaau aaggcuaguc    60
cguuaucaac uugaaaaagu ggcaccgagu cggugcuuuu                         100

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
tctaatacga ctcactata                                           19

<210> SEQ ID NO 21
<211> LENGTH: 61
<212> TYPE: DNA
<213> ORGANISM: Artificial Sequence
<220> FEATURE:
<223> OTHER INFORMATION: primer

<400> SEQUENCE: 21
tctaatacga ctcactatag ggcatcgact tcaaggagga gttttagagc tagaaatagc    60
a                                                              61

<210> SEQ ID NO 22
```

```
<211> LENGTH: 61
<212> TYPE: DNA
<213> ORGANISM: Artificial Sequence
<220> FEATURE:
<223> OTHER INFORMATION: primer

<400> SEQUENCE: 22
tctaatacga ctcactatag ggcatcgact tcaaggaaaa gttttagagc tagaaatagc      60
a                                                                      61

<210> SEQ ID NO 23
<211> LENGTH: 80
<212> TYPE: DNA
<213> ORGANISM: Artificial Sequence
<220> FEATURE:
<223> OTHER INFORMATION: primer

<400> SEQUENCE: 23
aaaagcaccg actcggtgcc acttttcaa gttgataacg gactagcctt attttaactt      60
gctatttcta gctctaaaac                                                  80

<210> SEQ ID NO 24
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: FAM
<222> LOCATION: (1)..(1)

<400> SEQUENCE: 24
aaaagcaccg actcggtgcc acttttt                                          27

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
gaggagctgt tcaccggg                                                    18

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cttgtacagc tcgtccatgc                                                  20

<210> SEQ ID NO 27
<211> LENGTH: 100
<212> TYPE: RNA
<213> ORGANISM: Artificial Sequence
<220> FEATURE:
<223> OTHER INFORMATION: primer

<400> SEQUENCE: 27
gaguccgagc agaagaagaa guuuuagagc uagaaauagc aaguuaaaau aaggcuaguc      60
cguuaucaac uugaaaaagu ggcaccgagu cggugcuuuu                           100
```

<210> SEQ ID NO 28
<211> LENGTH: 100
<212> TYPE: RNA
<213> ORGANISM: Artificial Sequence
<220> FEATURE:
<223> OTHER INFORMATION: primer

<400> SEQUENCE: 28
gaguccgagc agaagaauua guuuuagagc uagaaauagc aaguuaaaau aaggcuaguc    60
cguuaucaac uugaaaaagu ggcaccgagu cggugcuuuu                         100

<210> SEQ ID NO 29
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: SH
<222> LOCATION: (27)..(27)

<400> SEQUENCE: 29
tcttctgctc ggactcgcag aagattt                                       27

<210> SEQ ID NO 30
<211> LENGTH: 61
<212> TYPE: DNA
<213> ORGANISM: Artificial Sequence
<220> FEATURE:
<223> OTHER INFORMATION: primer

<400> SEQUENCE: 30
tctaatacga ctcactatag gagtccgagc agaagaagaa gttttagagc tagaaatagc    60
a                                                                   61

<210> SEQ ID NO 31
<211> LENGTH: 61
<212> TYPE: DNA
<213> ORGANISM: Artificial Sequence
<220> FEATURE:
<223> OTHER INFORMATION: primer

<400> SEQUENCE: 31
tctaatacga ctcactatag gagtccgagc agaagaatta gttttagagc tagaaatagc    60
a                                                                   61

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ctgtgtcctc ttcctgccct                                               20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ctctccgagg agaaggccaa                                            20

<210> SEQ ID NO 34
<211> LENGTH: 100
<212> TYPE: RNA
<213> ORGANISM: Artificial Sequence
<220> FEATURE:
<223> OTHER INFORMATION: primer

<400> SEQUENCE: 34
uaccuacggc aaauugugcu guuuuagagc uagaaauagc aaguuaaaau aaggcuaguc    60
cguuaucaac uugaaaaagu ggcaccgagu cggugcuuuu                        100

<210> SEQ ID NO 35
<211> LENGTH: 100
<212> TYPE: RNA
<213> ORGANISM: Artificial Sequence
<220> FEATURE:
<223> OTHER INFORMATION: primer

<400> SEQUENCE: 35
uaccuacggc aaauuguuuu guuuuagagc uagaaauagc aaguuaaaau aaggcuaguc    60
cguuaucaac uugaaaaagu ggcaccgagu cggugcuuuu                        100

<210> SEQ ID NO 36
<211> LENGTH: 59
<212> TYPE: DNA
<213> ORGANISM: Artificial Sequence
<220> FEATURE:
<223> OTHER INFORMATION: primer

<400> SEQUENCE: 36
taatacgact cactataggg tacctacggc aaattgtgct gtttcagagc tatgctgga    59

<210> SEQ ID NO 37
<211> LENGTH: 59
<212> TYPE: DNA
<213> ORGANISM: Artificial Sequence
<220> FEATURE:
<223> OTHER INFORMATION: primer

<400> SEQUENCE: 37
taatacgact cactataggg tacctacggc aaattgtttt gtttcagagc tatgctgga    59

<210> SEQ ID NO 38
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: SH
<222> LOCATION: (27)..(27)

<400> SEQUENCE: 38
caatttgccg taggtagcaa attgttt                                     27

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ggtgctgcga atggttgtgg                                                        20

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
cagcctcctc caaattccag c                                                      21

<210> SEQ ID NO 41
<211> LENGTH: 99
<212> TYPE: RNA
<213> ORGANISM: Artificial Sequence
<220> FEATURE:
<223> OTHER INFORMATION: primer

<400> SEQUENCE: 41
ggcaucgacu ucaaggagga guuuuagagc uagaaauagc aaauaaaaua aaaauaguau            60
guuuccaaag ugaauaauac guugcuggug gcugguauu                                   99

<210> SEQ ID NO 42
<211> LENGTH: 80
<212> TYPE: DNA
<213> ORGANISM: Artificial Sequence
<220> FEATURE:
<223> OTHER INFORMATION: primer

<400> SEQUENCE: 42
aataccagcc accagcaacg tattattcac tttggaaaca tactattttt attttatttt            60
gctatttcta gctctaaaac                                                        80

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
caaaggagac ctggagacga c                                                      21

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
cctaacaggc acccacatca                                                        20

<210> SEQ ID NO 45
<211> LENGTH: 22
<212> TYPE: DNA
<213> ORGANISM: Artificial Sequence
<220> FEATURE:
<223> OTHER INFORMATION: primer

<400> SEQUENCE: 45
cactgattca ttaggagctg gc                                                     22

```
<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
ctggattctg cagcagcaca ac                                              22

<210> SEQ ID NO 47
<211> LENGTH: 24
<212> TYPE: DNA
<213> ORGANISM: Artificial Sequence
<220> FEATURE:
<223> OTHER INFORMATION: primer

<400> SEQUENCE: 47
cactaatacg gttctgtaaa cgcc                                            24

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
ccttactatg tgctgggcac tg                                              22

<210> SEQ ID NO 49
<211> LENGTH: 23
<212> TYPE: DNA
<213> ORGANISM: Artificial Sequence
<220> FEATURE:
<223> OTHER INFORMATION: primer

<400> SEQUENCE: 49
cctgcagaca ggaatagccc tac                                             23

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
gcttcttatc cctgtcttcc agg                                             23

<210> SEQ ID NO 51
<211> LENGTH: 17
<212> TYPE: DNA
<213> ORGANISM: Artificial Sequence
<220> FEATURE:
<223> OTHER INFORMATION: primer

<400> SEQUENCE: 51
taatacgact cactata                                                    17

<210> SEQ ID NO 52
<211> LENGTH: 28
<212> TYPE: DNA
<213> ORGANISM: Artificial Sequence
```

```
<220> FEATURE:
<223> OTHER INFORMATION: primer

<400> SEQUENCE: 52
ttccttgaag tcgatgcctt caaggttt                                              28
```

NEAR-INFRARED PHOTOTHERMALLY ACTIVATED CRISPR/CAS9 GENOME EDITING MACHINE

CROSS REFERENCE TO RELATED APPLICATION

The instant application contains a Sequence Listing electronically in ASCII format and is hereby incorporated by reference in its entirety. The ASCII copy, created on Sep. 13, 2019, is named PAT 106796-2 Seq US non-prov_St25 and is 64 bytes in size.

FIELD

The present disclosure relates generally to a near-infrared photothermally activated CRISPR/CAS9 genome editing machine.

BACKGROUND

The CRISPR/Cas9 system has revolutionized genome engineering. It can edit any gene of interest simply by designing a single guide RNA (sgRNA) with a 20-nucleotide (nt) target binding domain to complement the sequence of the gene[1,2]. Because of its simplicity and versatility, the CRISPR/Cas9 system enables broad applications from basic biological research to therapeutic development[3,4]. However, its therapeutic applications are limited by two main challenges: efficiently delivering the system into target cells and minimizing off-target editing.

Viral delivery methods are often used to express sgRNA and Cas9 within target cells[5]. But the prolonged expression of sgRNA and Cas9 increases off-target genome modifications. Thus, many efforts are focused on developing non-viral techniques that directly deliver sgRNA and/or Cas9 into target cells. Lipids[6], polyethylenimine[7], and nanomaterials[8-13] have been examined as carriers to deliver sgRNA and Cas9. While these approaches are promising for delivery, there remains a need to efficiently release sgRNA from carriers toward development of human therapeutics[14-16].

To improve the CRISPR/Cas9 specificity and reduce off-target effects, researchers have developed several strategies, including engineering the Cas9 protein[17,18], modifying sgRNA[19], and using direct delivery to reduce the duration of Cas9 activity[20,21]. Another notable approach is to control and modulate the activity of the Cas9 system using external stimuli. Small molecules and ultraviolet-visible light have been used to control the activity of the Cas9 system through engineering the Cas9 protein or sgRNA[22-29]. However, the cellular location and concentration of exogenous small molecules are difficult to control, and UV-visible light does not efficiently penetrate tissues. Other methods for efficient and precise control of the CRISPR/Cas9 biotechnology are in demands.

SUMMARY

In one aspect there is provided an isolated protector polynucleotide for reversible binding to an sgRNA, consisting of or comprising the structure of Formula (I),

T-S-L           (I)

wherein,
T comprises a targeting sequencing domain polynucleotide that reversibly hybridizes to a target binding domain of an sgRNA;
S comprises a stem domain polynucleotide sequence that forms a hairpin structure when said protector polynucleotide is not bound to said sgRNA; and
L comprises linker polynucleotide sequence having a first end attached to said S, and a second end for attachment to a nanostructure.

In one example, said T is 13, 14, 15, 16, 17, or 18 nucleotides, in length.

In one example, said S is 6, 7, 8, or 9 nucleotides, in length.

In one example, L comprises a thiol moiety positioned at the 3' end.

In one aspect there is provided a system, comprising,
an isolated protector polynucleotide for reversible binding to an sgRNA, consisting of or comprising the structure of Formula (I),

T-S-L           (I)

wherein,
T comprises a targeting sequencing domain polynucleotide that reversibly hybridizes to a target binding domain of an sgRNA;
S comprises a stem domain polynucleotide sequence that forms a hairpin structure when said protector polynucleotide is not bound to said sgRNA; and
L comprises linker polynucleotide sequence having a first end attached to said S, and a second end for removable attachment to a support, and
a support attached to said second end of said L,
In one example, said T is 13, 14, 15, 16, 17, or 18 nucleotides, in length.

In one example, said S is 6, 7, 8, or 9 nucleotides, in length.

In one example, said support comprises a nanostructure.
In one example, said support comprises a noble metal.
In one example, said noble metal comprises a nanoparticle.
In one example, said noble metal is gold.
In one example, said support is a gold nanorod (AuNR).
In one aspect there is provided a method of editing a gene in a cell from a subject, comprising:
providing said cell with a Cas protein or Cas protein-encoding plasmid,
contacting said cell with a system of any one of claims 5 to 12 under conditions sufficient for uptake of said system in said cell, and
Irradiating said cell with a NIR laser.
In one example, said cell is a human cell.
In one example, said gene is EGFP, PLK1, or EMX1.
In one aspect there is provided a kit comprising an isolated protector polynucleotide for reversible binding to an sgRNA according to anyone of claims 1 to 4, a container, and optionally instructions for the use thereof.

In one aspect there is provided a kit comprising a system according to anyone of claims 5 to 15, a container, and optionally instructions for the use thereof.

BRIEF DESCRIPTION OF THE FIGURES

Embodiments of the present disclosure will now be described, by way of example only, with reference to the attached Figures.

FIG. 1A) A sgRNA is hybridized to a protector DNA that is conjugated on a gold nanorod (AuNR). NIR irradiation generates heat and activates the release of the sgRNA from the protector. After release of the sgRNA, the protector forms a hairpin structure to hinder re-hybridization of the sgRNA. FIG. 1B) AuNRs carry the protected sgRNA assembly into the cells. Irradiation of the cells with a NIR laser (808 nm) results in controlled release of the sgRNA inside the cells, initiating gene editing.

FIG. 2A) Percent of hybridized sgRNA to two protectors ($T_{16}S_8$ and $T_{16}S_0$) of same length, but with or without an 8-nt stem. FIG. 2B) Gel electrophoresis images showing the dsDNA substrate (702 bp) the and its CRISPR/Cas9 cleavage products (383 bp and 319 bp). Lane 1 from left: dsDNA substrate; lanes 2 and 3: dsDNA incubated with $T_{16}S_0$-LACM, before and after NIR irradiation; lane 4: dsDNA incubated with free sgRNA, serving as a positive control; lanes 5 and 6: dsDNA incubated with $T_{16}S_8$-LACM, before and after NIR (808 nm) irradiation.

FIG. 4A) Confocal images of A549-GFP/Cas9 cells (from left to right): untreated, treated with LACM but no NIR irradiation, treated with mutant LACM and with NIR irradiation, and treated with LACM and with NIR irradiation. FIG. 4B) Flow cytometry histograms of cells corresponding to treatments in FIG. 4A.

FIG. 5A) Lanes 1 to 4 represent A549 cells irradiated with NIR, treated with LACM but not NIR, treated with mutant LACM and NIR, and treated with EGFP-LACM or EMX1-LACM and irradiated with 808-nm NIR laser, respectively. FIG. 5B) Lanes 1 to 4 represent HEK293T cells without transfection of Cas9, cells not treated with LACM, cells treated with LACM but not with NIR irradiation, and cells treated with LACM and irradiated with 808-nm NIR laser, respectively.

FIG. 6A) Levels of the mRNA of PLK1. FIG. 6B) Western blotting results showing the levels of PLK1 protein. Bands from left to right (I-VI) were from the analyses of cells without treatment (I), cells treated with LACM but no NIR irradiation (II), cells treated with bare AuNR (III) and NIR irradiation, cells treated with LACM containing scrambled sgRNA sequences and with NIR irradiation (IV), cells treated with LACM containing a mutant sgRNA and with NIR irradiation (V), and cells treated with LACM and NIR irradiation (VI). FIG. 6C) Flow cytometry results showing percent of apoptotic cells in the top right quadrant. The mRNA quantification FIG. 6A and Western blotting analysis FIG. 6B were conducted after the cells were treated for two days. Flow cytometry FIG. 6C analysis was performed after the cells were treated for five days.

FIGS. 7A-7D. Design and sequences used in the laser activated CRISPR/Cas9 nano-machine (LACM). FIG. 7A) Sequence of the sgRNA for editing EGFP. FIG. 7B) Sequence of a protector oligonucleotide, consisting of a target-sequestering domain of 16 nucleotides ($T_{16}$), a stem domain of 8 nucleotides ($S_8$), and 3 thymine nucleotides with the last thymine thiolated for conjugation to the AuNR. The underlined stem sequences form a hairpin when the protector sequence is not hybridized to the sgRNA. FIG. 7C) The AuNR was conjugated with dozens of a protector DNA hybridized with the target binding domain of the sgRNA. One such protector-sgRNA hybrid is shown conjugated onto the AuNR. FIG. 7D) Processes of NIR laser-activated release of sgRNA from LACM. Irradiation of the LACM with a near-infrared laser produced heat, which dissociated the sgRNA from the protector strand. When separated from the sgRNA, the protector sequence formed spontaneously a hairpin structure, preventing it from re-hybridization with the sgRNA. The released sgRNA proceeded with CRISPR/Cas9 genome editing.

FIGS. 10A and 10B. Gel images showing products of hybridization reaction between the protector DNA and the sgRNA at 37° C. 1 μM sgRNA was mixed with two protector DNA sequences $T_{16}S_0$ and $T_{16}S_8$ at molar ratios of 1:1.5 and 1:2, respectively. The mixtures were incubated at 37° C. for varying durations of time (0.25-6 h), and then analyzed using PAGE.

FIGS. 28A and 28B. Controlled release of sgRNA from LACM in A549 cells after NIR irradiation. The FAM and TMR dual-labeled LACM was constructed using TMR-labeled protector and sgRNA hybridized with a FAM-labeled DNA at the 3'-end. The TMR-LACM was constructed using TMR-labeled protector and unlabeled sgRNA. A549 cells were incubated for 8 h in the Opti-MEM medium supplemented with the TMR labeled LACM or FAM and TMR dual-labeled LACM. The cells were imaged using fluorescence microscopy before (the third row) and after (the bottom row) the NIR irradiation (808 nm).

EMX1 On
(SEQ ID NO: 1)
GAGTCCGAGCAGAAGAAGAAGGG

EMX1 Off1
(SEQ ID NO: 2)
GAGgCCGAGCAGAAGAAagACGG

EMX1 Off2
(SEQ ID NO: 3)
GAGTCCtAGCAGgAGAAGAAGaG

EMX1 Off3
(SEQ ID NO: 4)
GAGTCtaAGCAGAAGAAGAAGaG

EMX1 Off4
(SEQ ID NO: 5)
GAGTtaGAGCAGAAGAAGAAAGG

Figure 30:
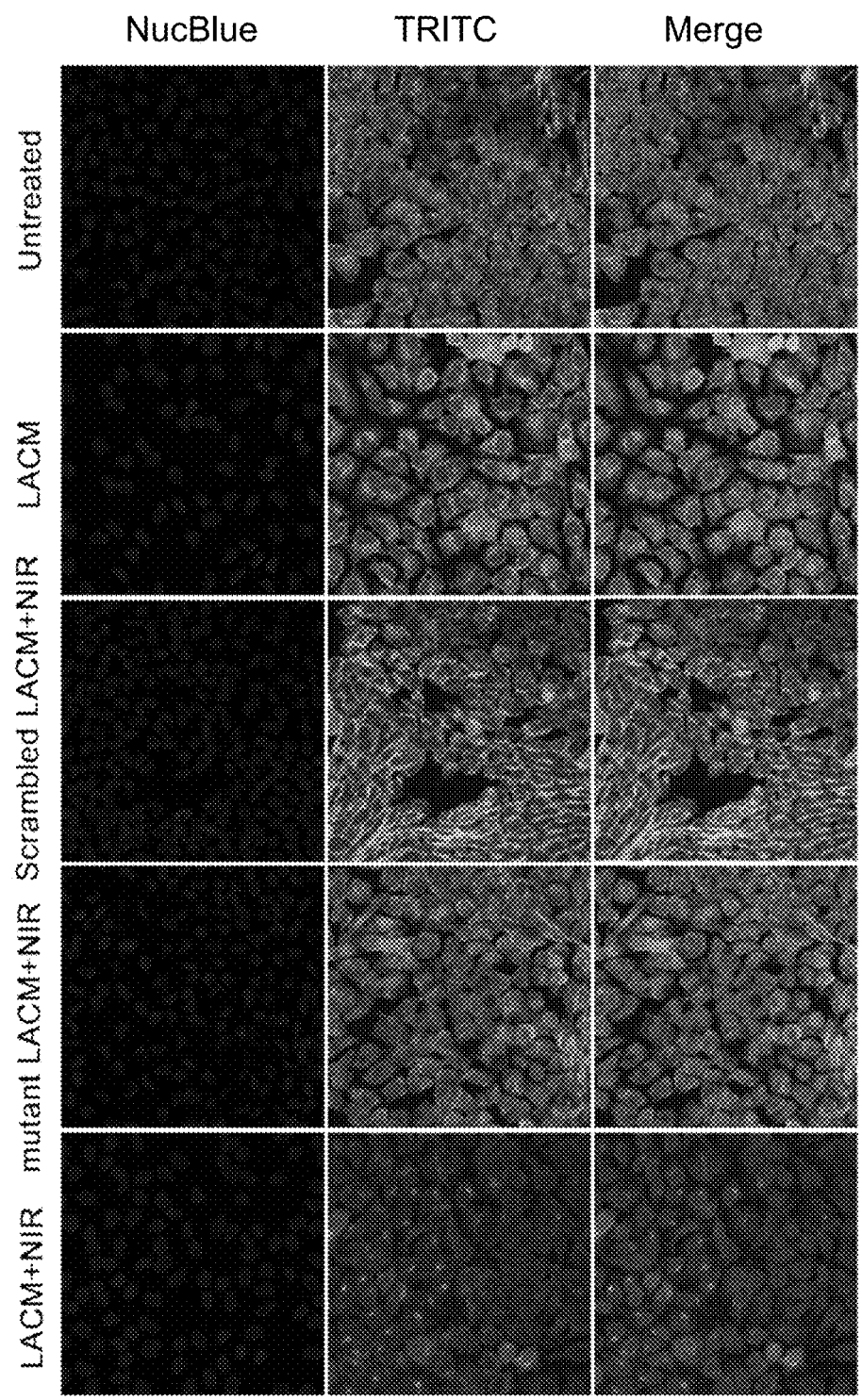

FIG. 30. Confocal images of A549 cells immunostained with antibody to the PLK1 protein. The first two sets of cells were either not treated or treated with LACM but not with NIR irradiation. The other three sets of cells were treated with LACM containing
scrambled sequence, LACM containing a mutant sgRNA, or LACM containing the correct sgRNA, all with NIR irradiation. After five days of incubation, the cells were fixed with PFA, and then incubated with PLK1 monoclonal antibody (#35-206, ThermoFisher). After removal of the unbound antibodies by washing, the goat anti-mouse IgG (H+L) cross-adsorbed secondary antibody with Alexa Fluor 546 (#A-11003, ThermoFisher) was added. The TRITC channel detects fluorescence of Alexa Fluor 546 and the the PLK1 protein. NucBlue stains nucleus of the cells. The lower TRITC fluorescence in the cells treated with LACM and MR irradiation (bottom row) indicates diminishing PLK1 protein in the cells.

DETAILED DESCRIPTION

Unless defined otherwise, all technical and scientific terms used herein have the same meaning as commonly understood by one of ordinary skill in the art to which this invention belongs.

Generally, there is described herein and a NIR laser-activated CRISPR/Cas9 nano-machine (LACM) and method(s).

Accordingly, in one aspect, there is described a CRISPR/Cas system and use of the same in editing a genome of a cell from a subject.

The term "subject", may refer to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The terms "CRISPR/Cas", "CRISPR/Cas system" and "nucleic acid-targeting system" may be used interchangeably. CRISPR/Cas systems are known in the art.

As is conventional in the art, the guide RNA, also referred to herein as a single guide RNA, sgRNA, or gRNA, guides a cognate Cas protein to specific sites in the genome for targeted cleavage.

As used herein, "cognate" refers to a Cas protein and a sgRNA that are capable of forming a nucleoprotein complex, which directly binds to a target nucleic acid molecule that is complementary to a nucleic acid sequence present in the sgRNA.

As used here, the term "cleavage" may refers to the generation of a break in the DNA. This may be either a single-stranded break or a double-stranded break depending on the type of nuclease that may be employed.

Accordingly, this system may be used to edit the genome of a cell of a subject.

As used herein, the term "edit", "editing", or "edited" refers to a method of altering a nucleic acid sequence of a polynucleotide (e.g., for example, a wild type naturally occurring nucleic acid sequence or a mutated naturally occurring sequence) by selective deletion of a specific genomic target or the specific inclusion of new sequence through the use of an exogenously supplied DNA template. Such a specific genomic target includes, but may be not limited to, a chromosomal region, mitochondrial DNA, a gene, a promoter, an open reading frame or any nucleic acid sequence.

The term "delete", "deleted", "deleting" or "deletion" as used herein, may be defined as a change in either nucleotide or amino acid sequence in which one or more nucleotides or amino acid residues, respectively, are, or become, absent.

The term "gene of interest" as used herein, refers to any pre-determined gene for which deletion may be desired.

The term "polynucleotide" or "nucleic acid sequence" or "nucleic acid molecule" refers to a DNA or RNA molecule in single or double stranded form. In one example, a polynucleotide comprises a DNA encoding a protein or protein fragment.

The terms "protein" or "polypeptide" are used interchangeably and refer to molecules consisting of a chain of amino acids, without reference to a specific mode of action, size, three-dimensional structure or origin.

As used herein, the terms "target sequence" or "target site" refer to a nucleotide sequence (for example the "specific sites" mentioned above) against which a sgRNA capable of hybridizing.

In one example, a target sequence may comprise a coding nucleic acid sequence.

In other example, a target sequence may comprise a non-coding nucleic acid sequence.

As used herein, a "non-coding nucleic acid" may refer to encoding a functional RNA (e.g. transfer RNA, ribosomal RNA, microRNA, Piwi-interacting RNA), a promoter, an intron, an untranslated region of an mRNA (e.g., a 5' untranslated region or a 3' untranslated region), a pseudogene, a repeat sequence, or a transposable element. Non-coding sequences do not encode functional polypeptides.

In other example, a target sequence may be located in a promoter.

In other example, a target sequence may comprise a enhancer sequence.

In other example, a target sequence may comprise both a coding nucleic acid sequence and a non-coding nucleic acid sequence.

In one example, a target sequence provided herein is recognized and cleaved by a double-strand break inducing agent, such as a system comprising a CRISPR enzyme and a sgRNA.

In some examples, a sgRNA target site may have substantial sequence identity to the corresponding target site in the host cell genome (i.e., at least about 90%, 91%, 92%, 93%, 94%, 95%, 96%, 97%, 98%, 99% or complete sequence identity to the target site in the host cell genome).

The term "complementarity" refers to the ability of a nucleic acid molecule to form hydrogen bond(s) with another nucleic acid molecule (e.g., through traditional Watson-Crick base-pairing). A percent complementarity indicates the percentage of residues in a nucleic acid molecule that can form hydrogen bonds with a second nucleic acid sequence. When two polynucleotide sequences have 100% complementary, the two sequences are perfectly complementary, i.e., all of the contiguous residues of a first polynucleotide hydrogen bond with the same number of contiguous residues in a second polynucleotide.

LACM enables efficient delivery of single-guide RNA (sgRNA) into living cells and achieving controlled release of the sgRNA for the CRISPR/Cas9 activity.

In a specific example, LACM incorporates a nucleic acid assembly on gold nanorod (AuNR), achieving the benefits of efficient cellular uptake and surface thermal effects induced by a near-infrared (NIR) laser.

In one example, LACM incorporates a nucleic acid assembly on a support (which may also be referred to as a carrier), achieving the benefits of efficient cellular uptake and surface thermal effects induced by a near-infrared (NIR) laser. In some examples, the support is a noble metal. In a specific example, the support is a gold nanoparticle. In a further specific example, the support is a gold nanorod.

Given its improved delivery of sgRNA capabilities, the CRISPR/Cas system of described herein may be used in gene therapy, drug screening, genetic recording, genetic circuitry, disease diagnosis, or/and disease prognosis.

In one example, A LACM is constructed on gold nanorod (AuNR) carrier. A protector DNA is designed to stably hybridize with the target binding domain of sgRNA. Approximately 60 molecules of this hybridized duplex are anchored on each AuNR. The stable hybrid between the protector DNA and the sgRNA keeps the sgRNA on the AuNR, preventing the sgRNA from binding to the target gene. When the sgRNA is in this protected form, the Cas9 system is inactive despite that the LACM is taken up by the cells. Upon irradiation with a NIR laser, the localized surface plasmon resonance on the AuNR surface generates heat. The heat denatures the hybrid between the protector DNA and the sgRNA, releasing the sgRNA from AuNR. Once the sgRNA is thermally released from the protector DNA, the protector DNA forms a hairpin structure, preventing the released sgRNA from re-hybridizing to the protector DNA. The released sgRNA then binds to the Cas9 protein inside the cells, initiating the processes of editing specific genes.

In one example, the EGFP gene was edited.
In one example, the EMX1 gene was edited.
In one example, the PLK1 gene was edited.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Example 1: A CRISPR/Cas9 Genome Editing Nanomachine Activated by Near-Infrared Illumination The RNA-guided CRISPR/Cas9 system is a powerful genome-editing technology with broad applications. Improving delivery efficiency and controllable activity of the CRISPR/Cas9 system is an area of intense research. We report the construction and application of a CRISPR/Cas9 nano-machine (LACM), activated by near-infrared (NIR) laser, which enables efficient delivery of single-guide RNA (sgRNA) into living cells and achieves controlled release of the sgRNA for the CRISPR/Cas9 activity. The LACM was constructed using gold nanorod (AuNR) as a carrier that was decorated with dozens of protector DNA stably hybridizing with the target binding domain of sgRNA. The DNA assembly on the AuNR protected the sgRNA. Irradiation with a NIR laser generated heat on AuNR, resulting in controlled release of sgRNA, which guided CRISPR/Cas9 genome editing. Successful editing of the EGFP and EMX1 genes in A549 and HEK293T cells, as well as knocking down the PLK1 gene to induce apoptosis of the target cells, highlights promising potential of LACM for diverse applications.

We report here the concept and construction of a NIR laser-activated CRISPR/Cas9 nano-machine (LACM), enabling efficient delivery of sgRNA into living cells and achieving precise release of sgRNA inside the cells to function with the CRISPR/Cas9 system. We also demonstrate successful editing of the EGFP and EMX1 genes in A549 and HEK293T cells using the LACM strategy. We further show editing of the PLK1 gene and the resulting apoptosis of the target cancer cells.

Results and Discussion

Principle of Laser-Activated CRISPR/Cas9 Nano-Machine (LACM).

Figure 1A:
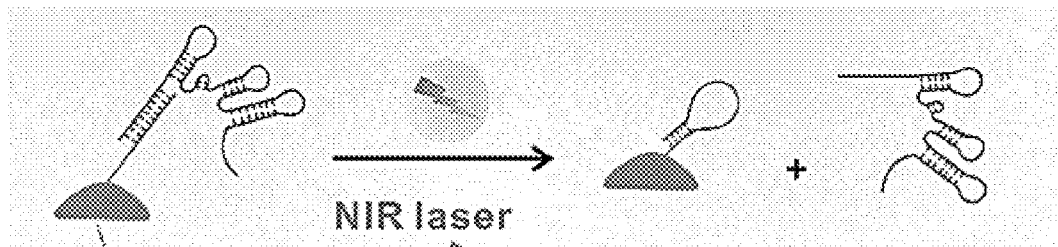
FIGS. 1A and 1B. Delivery and intracellular activation of a CRISPR/Cas9 genome editing nano-machine, activated by a near-infrared laser.
Figure 1B:
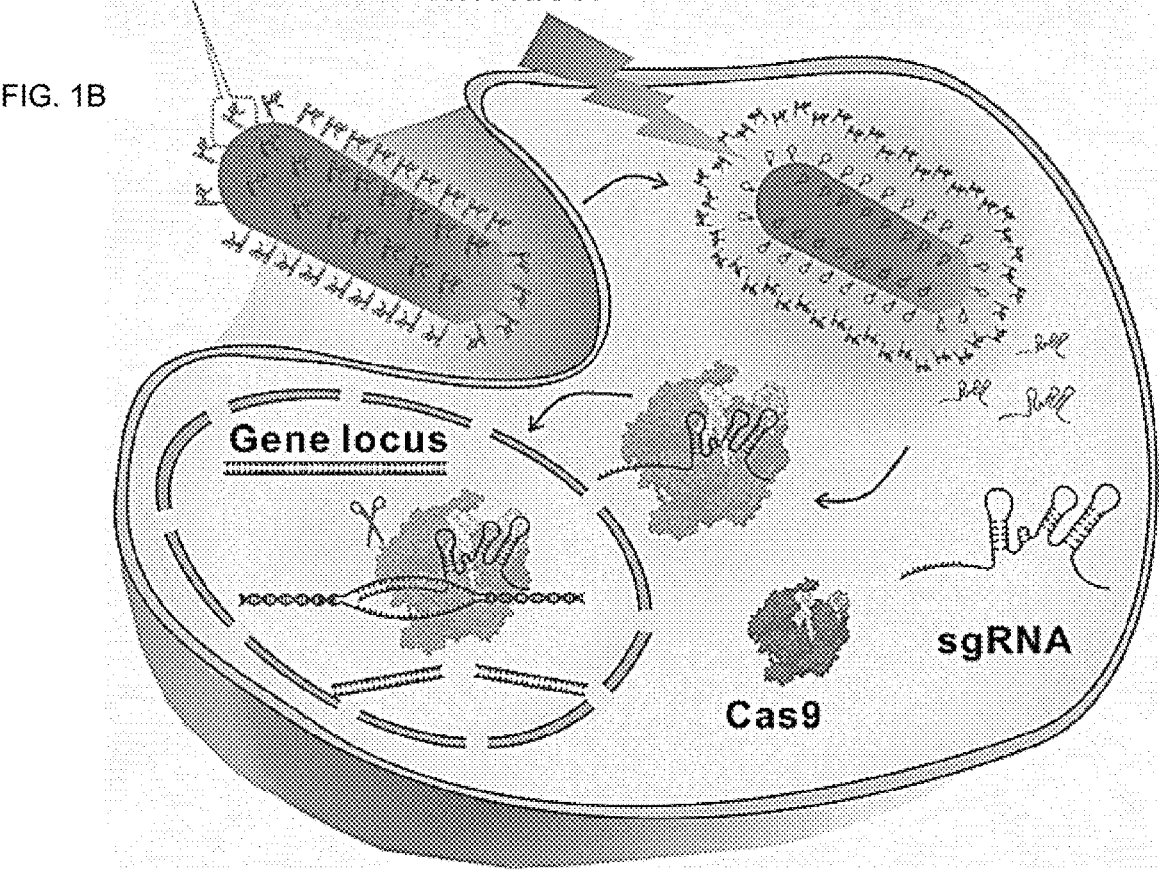

FIG. 1 depicts the overall concept and the intracellular operation of LACM. We used a 10×40 nm gold nanorod (AuNR) as the carrier to build the LACM because AuNR can be readily functionalized with DNA[30-32], enters cells with no need for transfection agents[33-34], and efficiently absorbs NIR to generate heat[35]. We designed a protector DNA according to the sequence of a sgRNA, so that the target binding domain of the sgRNA can hybridize to the protector DNA. We annealed the sgRNA to the protector strand, and then conjugated several dozen copies of the protector strand onto each AuNR, thereby achieving assembly of the sgRNA on the AuNR. The stable hybrid between the protector DNA and the sgRNA keeps the sgRNA on the AuNR, preventing the sgRNA from binding to the target gene. With this protected form of sgRNA, the Cas9 system is inactive despite that the LACM is taken up by the cells. Upon irradiation with a NIR laser, the localized surface plasmon resonance on the AuNR surface generates heat. The heat denatures the hybrid between the protector DNA and sgRNA, releasing the sgRNA from AuNR. To prevent the re-hybridization of sgRNA to the protector DNA after stop of irradiation, we designed the protector DNA to form a hairpin structure after release of sgRNA. The released sgRNA then binds to the Cas9 protein inside the cells, initiating the editing of specific genes.

Construction and Characterization of LACM.

We first constructed a LACM targeting EGFP stably expressed in A549 cells. Editing of EGFP terminates transcription of the green fluorescence protein (GFP), leading to decreases in fluorescence of the cells. The protector DNA of LACM (FIG. 7) serves three functions: 1) forming a stable hybrid with sgRNA; 2) efficiently dissociating from sgRNA after irradiation with a low-power NIR laser that does not affect the viability of the cells; 3) preventing the re-hybridization of sgRNA after its release. We designed the protector DNA to consist of a target-sequestering domain (T), a stem domain (S), and three thymine nucleotides with the last thymine thiolated for conjugation to the AuNR. Domain T is designed to hybridize to the target-binding domain of sgRNA. Domain S is design to allow the protector to form a hairpin structure when the sgRNA is released from the protector. We used a 3-nt linker to keep the assembly close to the surface of AuNR to be heated by NIR laser at a dose as low as possible.

We examined the efficiency of hybridizing sgRNA to six protectors containing domain T of 13, 14, 15, 16, 17, or 18-nt (Table 1). Gel electrophoresis analyses (FIG. 8) show that when domain T is longer than 15 nt, sgRNA is completely hybridized to the protector DNA and there is no detectable free sgRNA. We estimated the Gibbs free energy (ΔG) of hybridization between sgRNA and the protector having 16-nt. The ΔG is −31 kcal/mol, which is the approximate free energy required for completely sequestering the sgRNA.

Figure 2A:
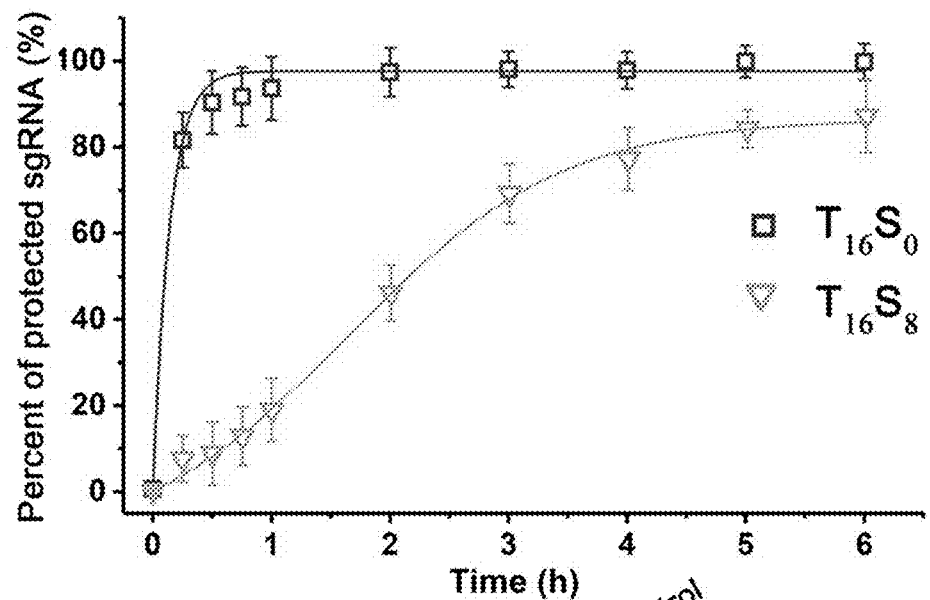
FIGS. 2A and 2B.
Figure 9:
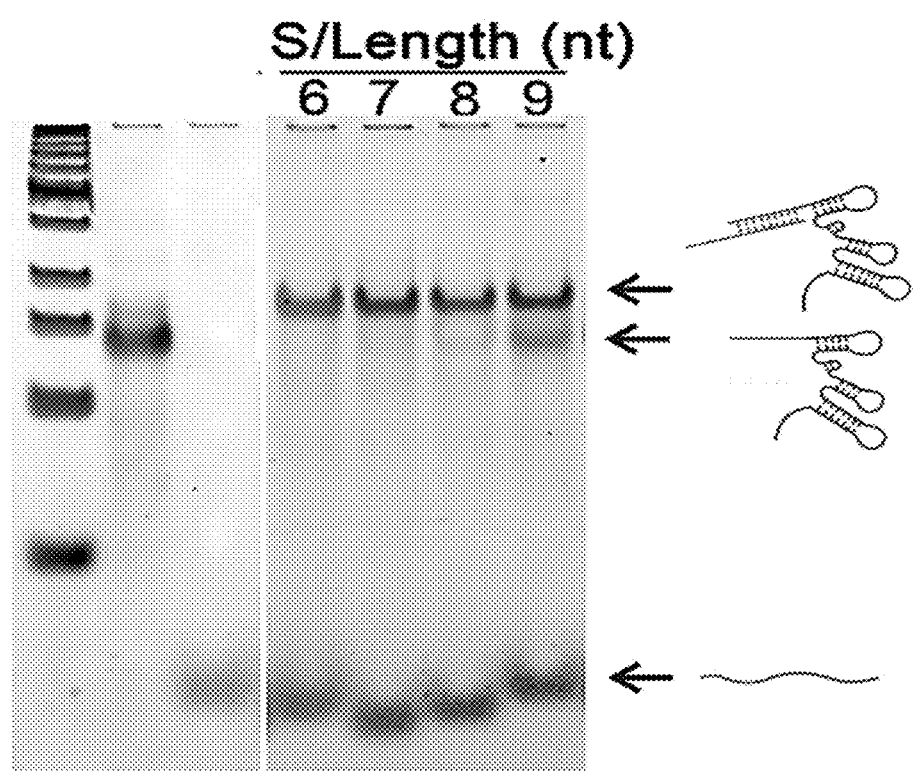
FIG. 9. Gel electrophoresis images showing formation of a duplex between the sgRNA and protectors containing different lengths of stem domain (S). From left to right Lane 1 to Lane 7. Lane 1: DNA ladder; lane 2: sgRNA; lane 3: protector DNA; lanes 4-7: mixture of sgRNA and protector with the stem domain (S) length from 6 to 9 nt. Gel electrophoresis analyses show that the sgRNA is completely hybridized to the protectors with S domain of 6-8 nt.

We also tested hybridization of the sgRNA to four protectors containing domain S of 6, 7, 8 or 9-nt, and found that the sgRNA is completely hybridized to the protectors with domain S of 6-8 nt (FIG. 9). The purpose of domain S in the protector is to form a hairpin structure after the sgRNA is released so that the released sgRNA would not re-hybridize to the protector. We compared two protectors of the same length, one with a sequence to form an 8-nt stem ($S_8$) and the other not forming a stem ($S_0$). FIG. S4 show that the sgRNA was readily re-hybridized to the protector that did not contain a stem sequence ($T_{16}S_0$), whereas the same sgRNA was not fully hybridized to the protector that contained an 8-nt stem sequence ($T_{16}S_8$). The hybridization rate between the sgRNA and protector $T_{16}S_0$ was $1.3\times10^6$ M$^{-1}$ and it was $0.27\times10^6$ M$^{-1}$ h$^{-1}$ between the sgRNA and protector $T_{16}S_8$, representing a reduction by 4.8 fold (FIG. 2a).

Figure 2B:
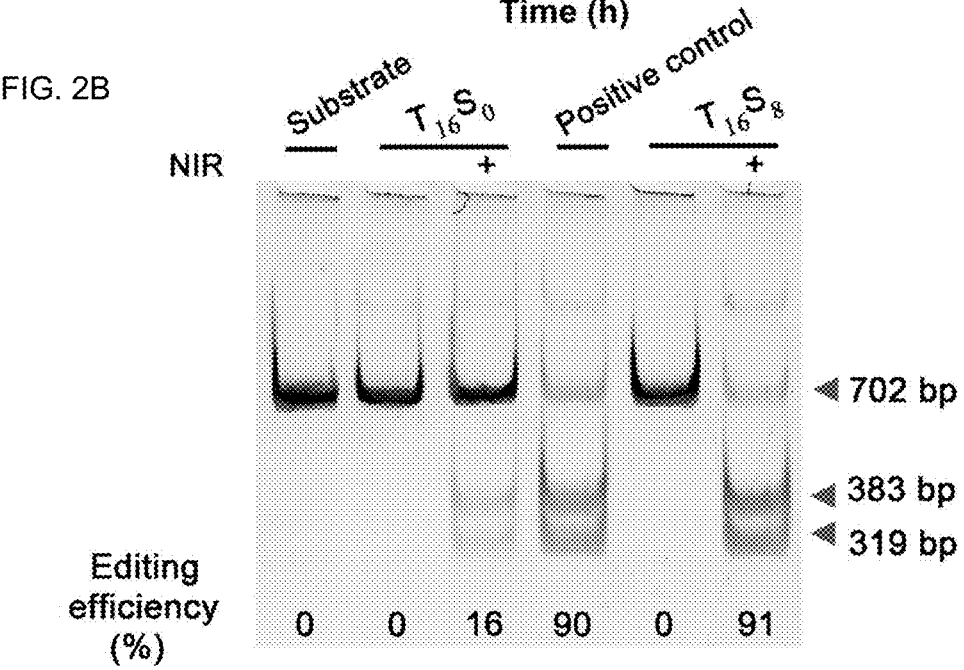
Figure 11:
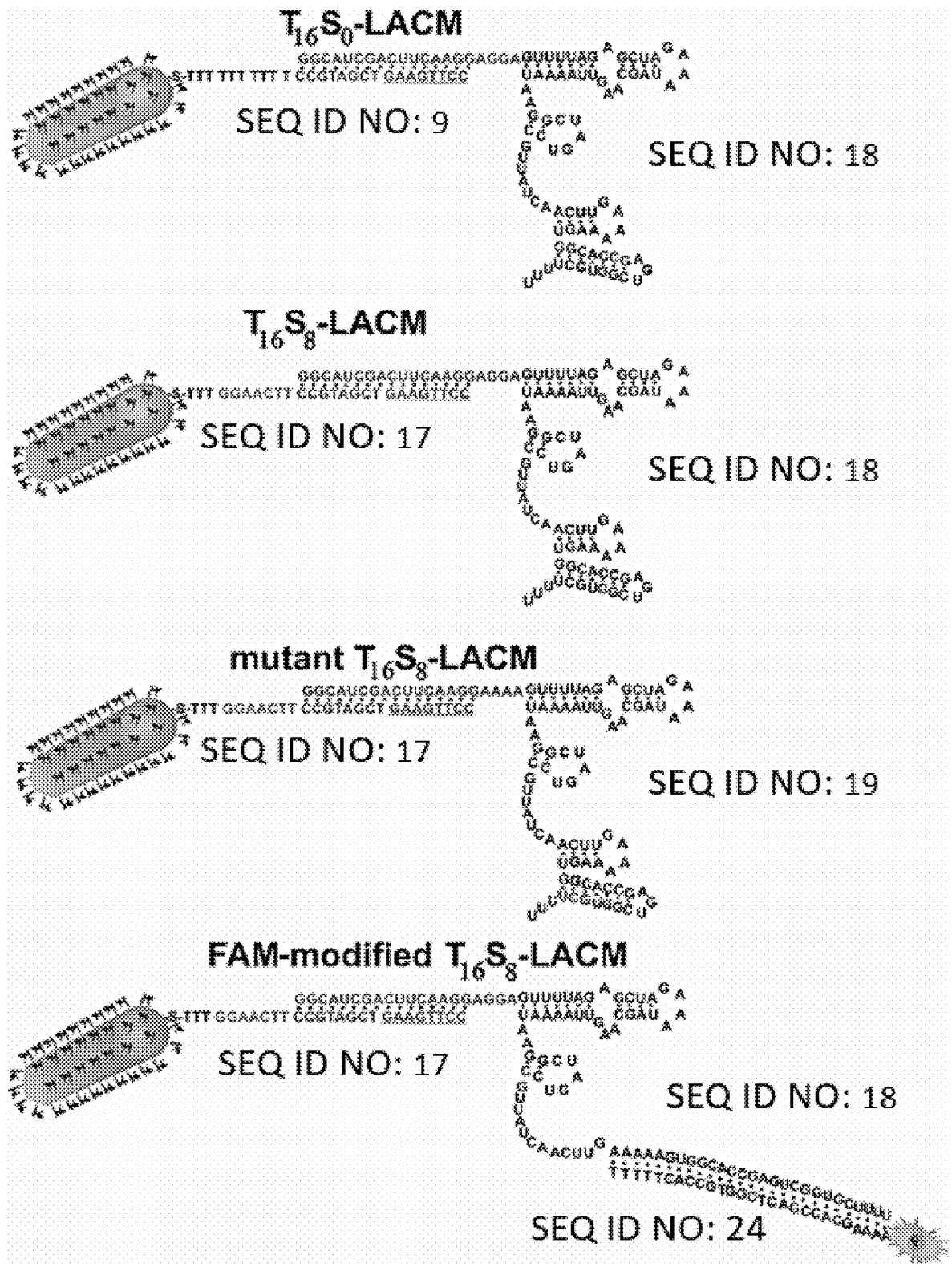
FIG. 11. Design and sequences used in the construction of four LACMs. $T_{16}S_0$-LACM and $T_{16}S_8$-LACM differ by the sequences of 8-nt that either form a hairpin ($T_{16}S_8$) or not forming a hairpin ($T_{16}S_0$). The mutant LACM was derived from the $T_{16}S_8$-LACM and contained two mutated nucleotides (AA instead of GG) as compared to the sequence of the sgRNA. The FAM-modified $T_{16}S_8$-LACM was based on the sequence of $T_{16}S_8$-LACM, but was hybridized with a fluorescent FAM-labeled strand at the 3'-end of the sgRNA.
Figure 12:
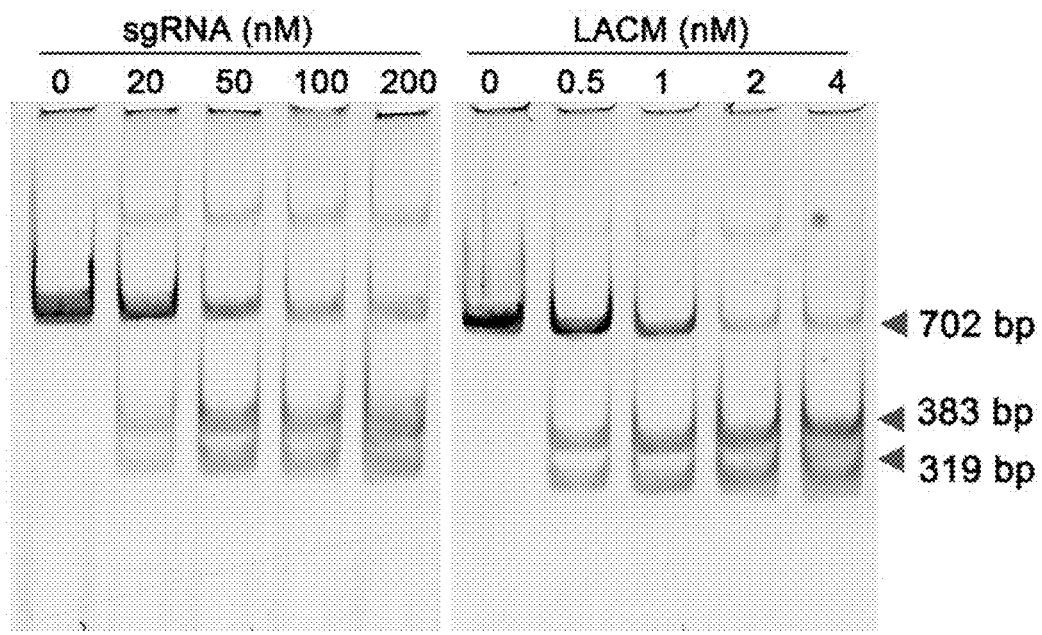
FIG. 12. Gel images showing products of Cas9-catalyzed cleavage of dsDNA substrate using either free sgRNA (20-200 nM) or the $T_{16}S_8$-LACM construct (0.5-5 nM). Both the free sgRNA and the LACM construct performed well with Cas9 to cleave the dsDNA substrate (702 bp) to two dsDNA products (383 bp and 319 bp).

We constructed $T_{16}S_8$-LACM and $T_{16}S_0$-LACM (FIG. 11) using protectors $T_{16}S_8$ and $T_{16}S_0$, and compared their performance of cleaving a double-stranded (ds) DNA substrate (702 bp). The CRISPR/Cas9-catalyzed cleavage products are two dsDNA fragments (383 bp and 319 bp). FIG. 2b shows no cleavage products from the treatment with $T_{16}S_8$-LACM or $T_{16}S_0$-LACM when NIR laser irradiation was not applied. These results suggest that the sgRNA is completely sequestered on the AuNR by hybridizing to the protector. When the NIR laser irradiation at 808 nm was applied, $T_{16}S_8$-LACM led to cleavage of 91% of the substrate, which was about 5.7-fold higher than that (16%) obtained with $T_{16}S_0$-LACM. These results further support that the 8-nt stem sequence in the protector greatly increases the release efficiency of sgRNA from LACM and prevents the released sgRNA from re-hybridizing to the protector. Consequently, Cas9 performed equally well with both the free sgRNA and $T_{16}S_8$-LACM to cleave the dsDNA substrate (FIG. 12).

Figure 13:
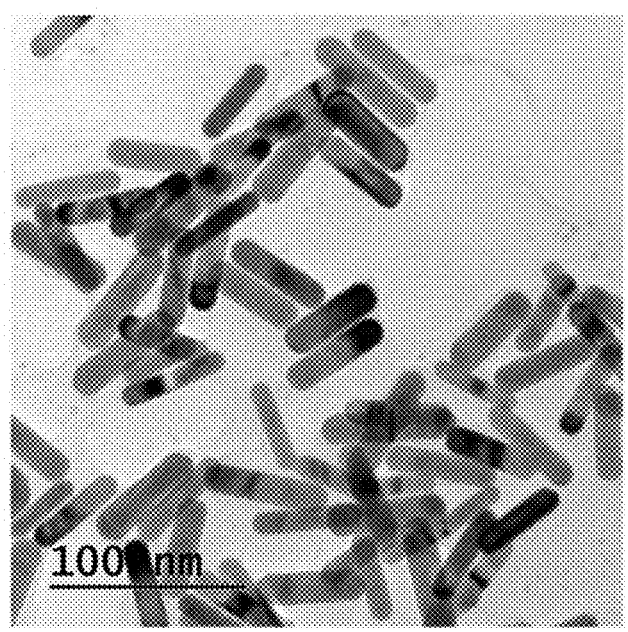
FIG. 13. Transmission electron microscopy (TEM) image of LACM. The scale bar is 100 nm. TEM image shows that AuNR remained uniform in shape and size after conjugation of the protector-sgRNA hybrids.
Figure 14:
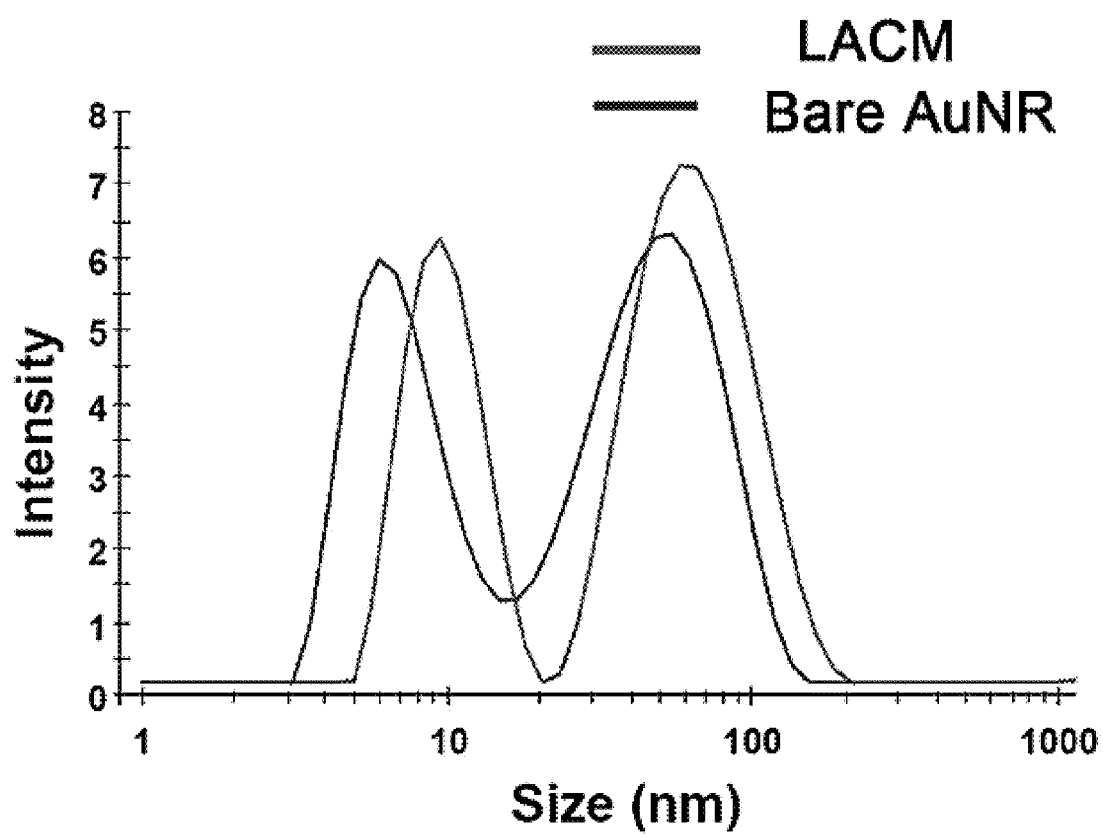
FIG. 14. Dynamic light scattering (DLS) analysis of the bare AuNR and LACM. DLS results show that the conjugation of the protector-sgRNA hybrids increased the hydrodynamic size of AuNR.
Figure 15:
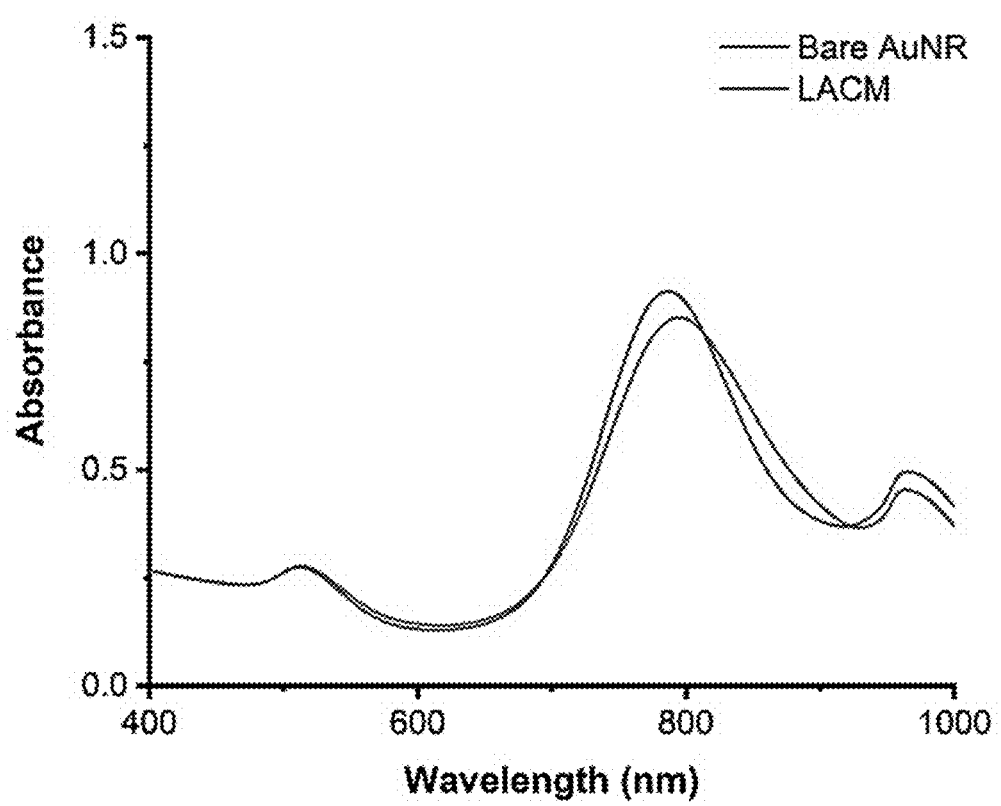
FIG. 15. Ultraviolet/Visible absorbance spectra of bare AuNR and LACM. Similar absorbance spectra with maximum absorbance at ~800 nm suggests that there is no aggregation of either the bare AuNR or the LACM construct.

We characterized the LACM using transmission electron microscopy, dynamic light scattering, and UV/Visible absorption (FIGS. 13-15). These results show that AuNR remained uniform in shape and size after conjugation of the protector-sgRNA hybrids, and that the conjugation of the protector-sgRNA hybrids increased the hydrodynamic size and negative surface charge of AuNR.

Figure 27:
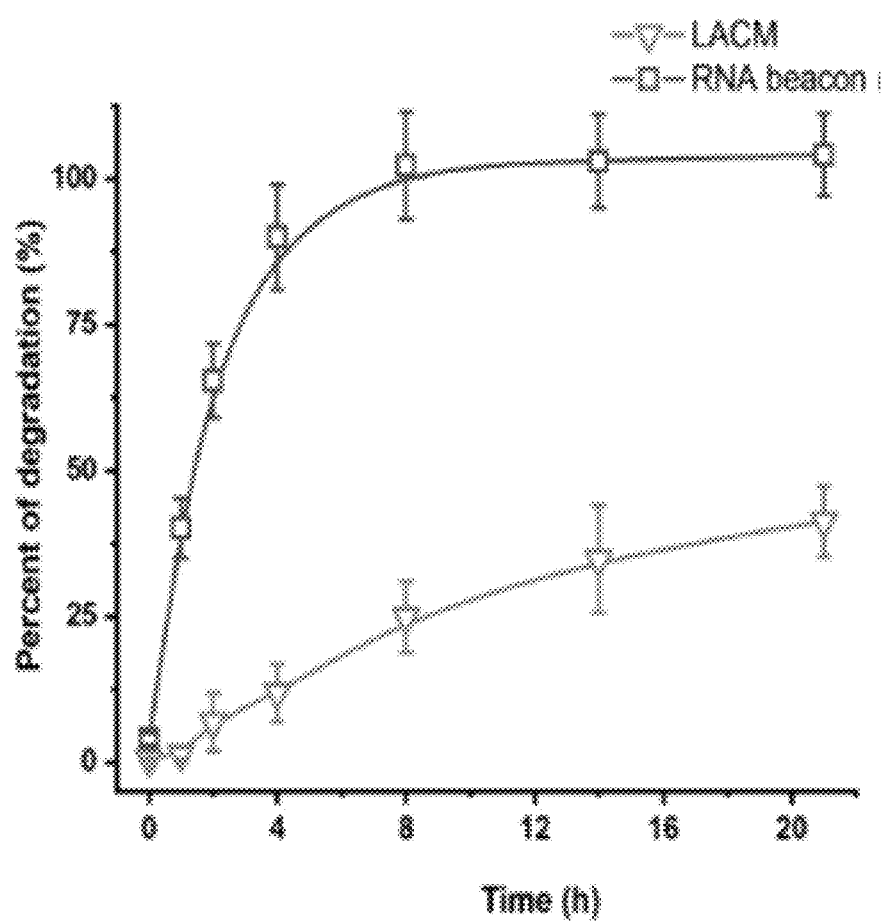
FIG. 27. Comparison of the stability of sgRNA on AuNR with that of a free RNA. FAM-labeled LACM was constructed using sgRNA hybridized with a FAM-labeled DNA similar to that shown in FIG. 18a. RNA beacon, representing RNA not constructed on the LACM, was used for comparison. A set of solutions containing 0.5 nM FAM-LACM or 20 nM of a RNA beacon (from Rnase Alert Kit) were prepared in the Opti-MEM medium. At each incubation time point (0, 1, 2, 4, 6, 8, 14, or 21 hours), a pair of solutions were centrifuged at 12000 rpm for 10 min. The fluorescence of supernatants was determined as a measure of the degraded (cleaved) sgRNA or RNA beacon.

We examined the stability of sgRNA in the LACM construct (FIG. 27). Approximately 25% of sgRNA in the LACM construct was degraded after 8 h of incubation in the cell medium. This is compared to complete degradation of the free RNA in the same medium. Therefore, conjugation of sgRNA onto AuNR improved the stability of the sgRNA, which is consistent with previous findings on the improved stability of DNA after conjugation to gold nanoparticles.[36-38]

Direct Delivery of LCAM into Cells and Release of sgRNA Inside the Cells.

Figure 3:
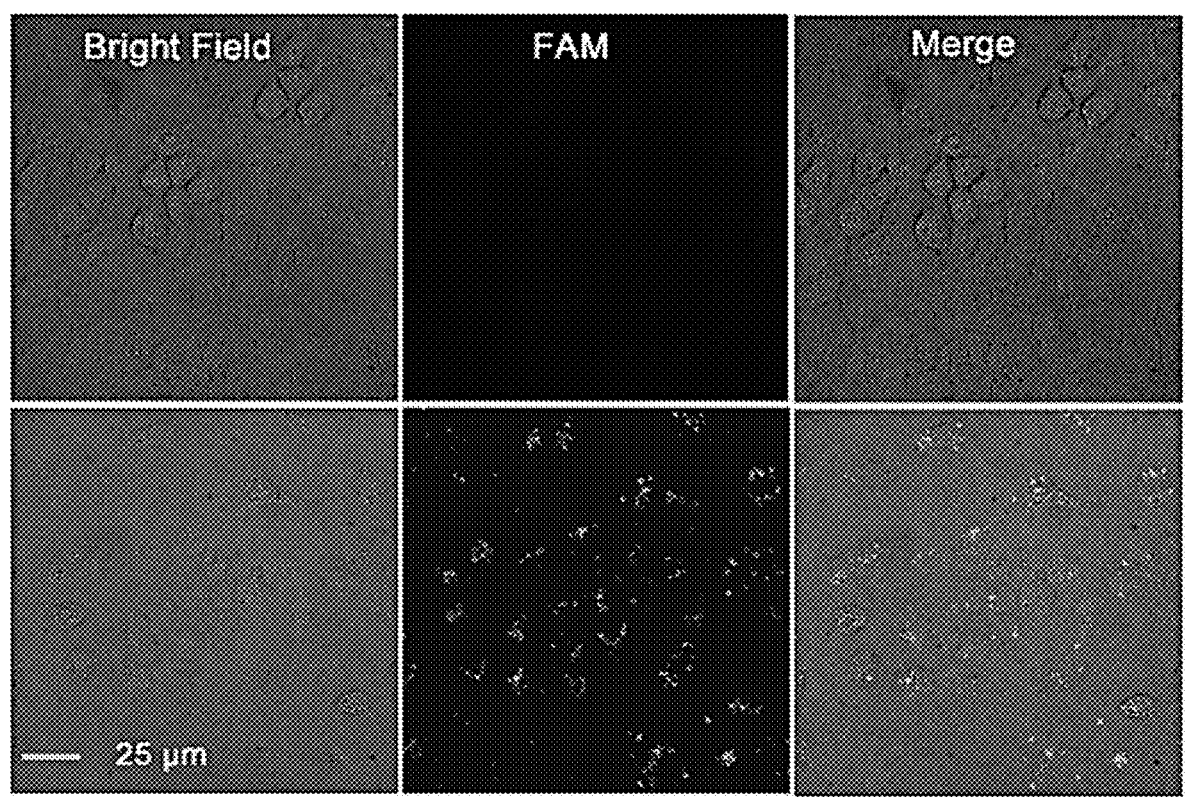
FIG. 3. Confocal images of the untreated A549 cells (top) and the A549 cells treated with FAM-modified $T_{16}S_8$-LACM (bottom).
Figure 16:
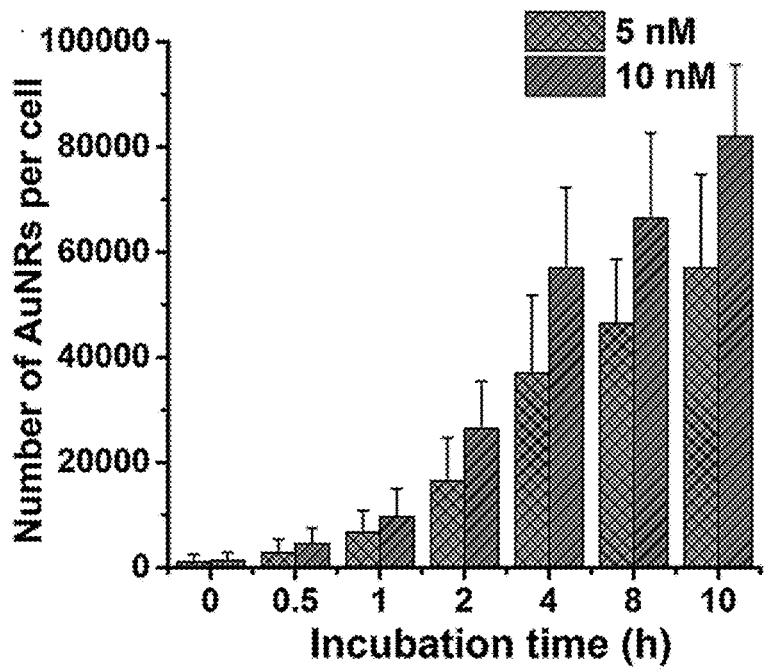
FIG. 16. Average number of AuNRs per cell estimated by detecting Au using inductively coupled plasma mass spectrometry (ICP-MS). A549 cells were incubated with 5 nM and 10 nM LACM for 10 h, without using any transfection reagents. Cellular uptake of LACM over time was determined using ICP-MS. Cells incubated with 5 nM
LACM for 10 h contained about $4.6 \times 10^4$ LACM per cell on average, which is equivalent to 18.2 nM concentration inside the cells and is 3.6-fold higher than the incubation concentration outside the cells. With each LACM containing 60 sgRNA strands, the concentration of sgRNA inside the cell is equivalent to 1.1 µM ($60 \times 18.2$ nM).
LACM for 10 h contained about $4.6 \times 10^4$ LACM per cell on average, which is equivalent to 18.2 nM concentration inside the cells and is 3.6-fold higher than the incubation concentration outside the cells. With each LACM containing 60 sgRNA strands, the concentration of sgRNA inside the cell is equivalent to 1.1 µM ($60 \times 18.2$ nM).

We determined the delivery of LACM to A549 cells, by monitoring the fluorescently modified LACM in the cells. The cells treated with the FAM-modified $T_{16}S_8$-LACM clearly show fluorescence (FIG. 3), indicating uptake of the fluorescently labeled LACM. We also determined the average number of AuNRs in the cells by detecting Au using inductively coupled plasma mass spectrometry (ICP-MS) (FIG. 16). Cells incubated with 5 nM LACM for 10 h contained about $4.6\times10^4$ LACM per cell on average, which is equivalent to 18.2 nM concentration inside the cells and is 3.6-fold higher than the concentration in the incubation medium. With each LACM containing 60 sgRNA strands, the concentration of sgRNA inside the cell is equivalent to 1.1 μM (60×18.2 nM). These results indicate efficient delivery of LACM and its associated sgRNA.

Figure 28B:
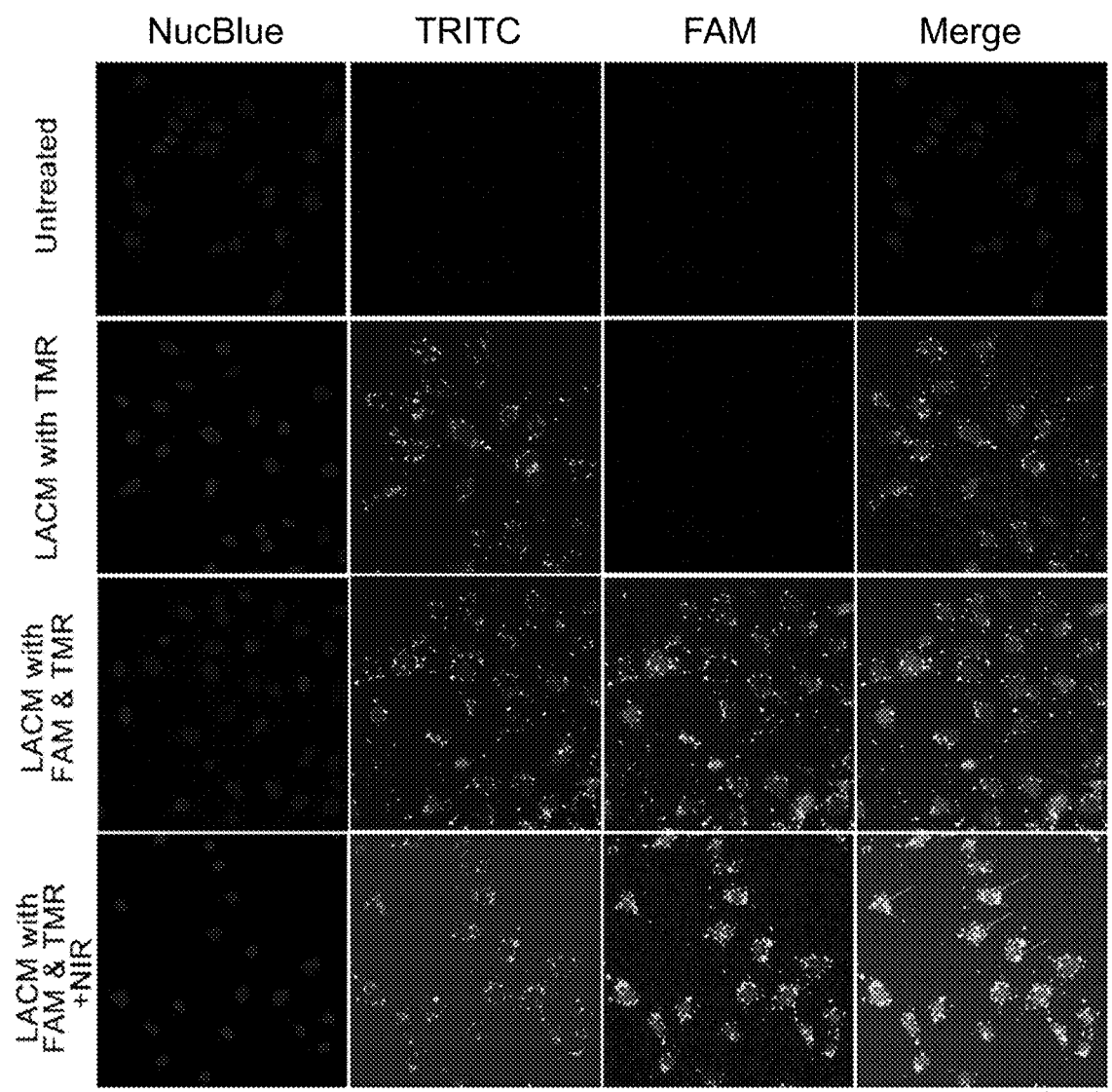

We then studied the release of sgRNA from LACM inside the cells after irradiation with the NIR laser (FIG. 28). We labeled the protector DNA with TMR and the complementary strand hybridized to sgRNA with FAM (FIG. 28a). The overlapping green (FAM) and orange (TMR) fluorescence signals inside the cells after 8-h incubation indicate uptake of LACM. After NIR irradiation, the green fluorescence from FAM is increased and the orange fluorescence from TMR is decreased (FIG. 28b, bottom panel). These results are consistent with the principle of the activated release of sgRNA from LACM. The increase in the green fluorescence of FAM is because of the increased distance of FAM from AuNR, whereas the decrease in orange fluorescence of TMR is due to the formation of the hairpin that places TMR closer to AuNR (FIG. 28a). The strong green fluorescence of FAM and low orange fluorescence of TMR in the nucleus suggest endosomal escape of LACM and efficient transporting of sgRNA into the nucleus.

Figure 17:
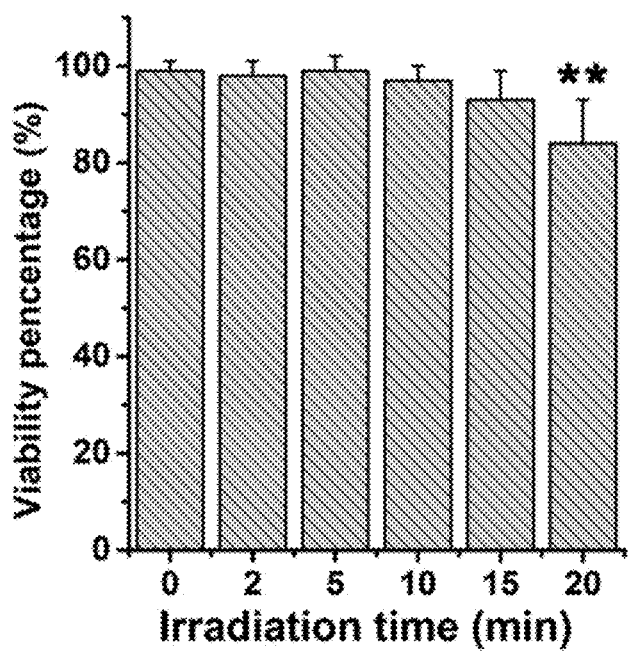
FIG. 17. Cell viability after incubation with LACM and NIR irradiation (808 nm) for various durations of time. Cell viability was assessed after irradiation with a NIR laser (808 nm) for 0-20 min. Irradiation time under 15 min did not significantly affect the cell viability. ** denotes p<0.01 from a t-test comparing data of adjacent time points.
Figure 18:
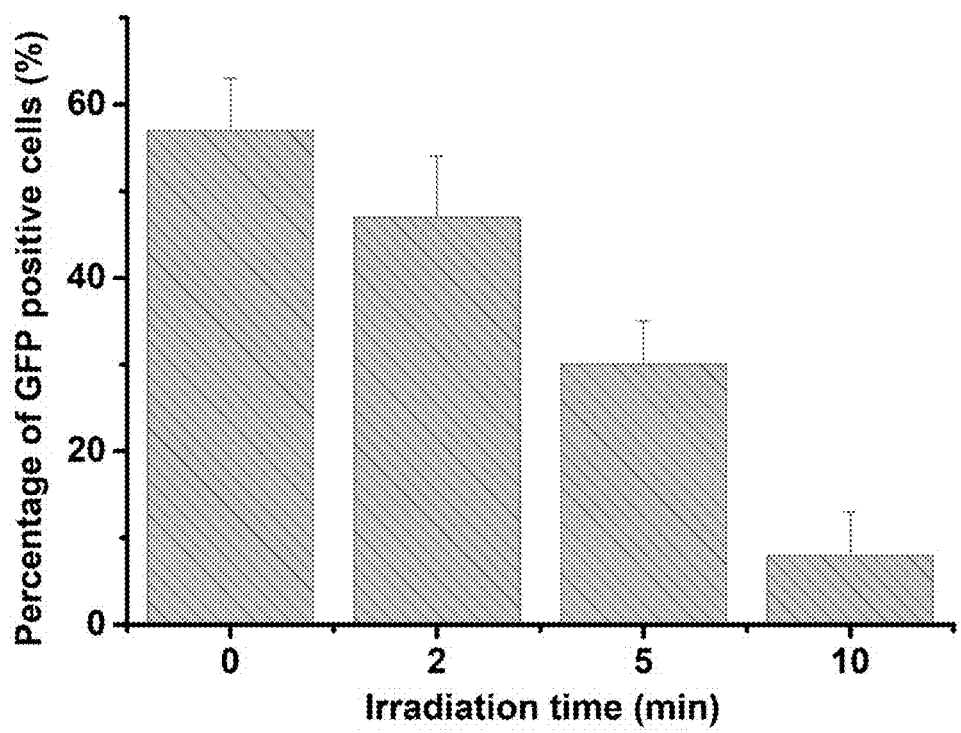
FIG. 18. Effect of NIR laser (808 nm) irradiation time of LACM on editing of the EGFP gene in A549 cells. A549-GFP/Cas9 cells stably expressing GFP and Cas9 proteins were used in this experiment. The cells were incubated with 5 nM of LACM for 10 h, and then irradiated for varying durations of time. After cell growth for 5 days, the cells were washed, trypsinized, pelleted, and re-suspended in PBS buffer containing 2% FBS. Flow cytometry was used to analyze fluorescent cells. Highly fluorescent cells represent those containing GFP proteins. Decreases in percentage of highly fluorescent cells indicate successful editing of the EGFP gene in the cells, resulting in decreases in expression of GFP protein. Error bars represent one standard deviation from triplicate cell incubation/treatment experiments (n=3).
Figure 19:
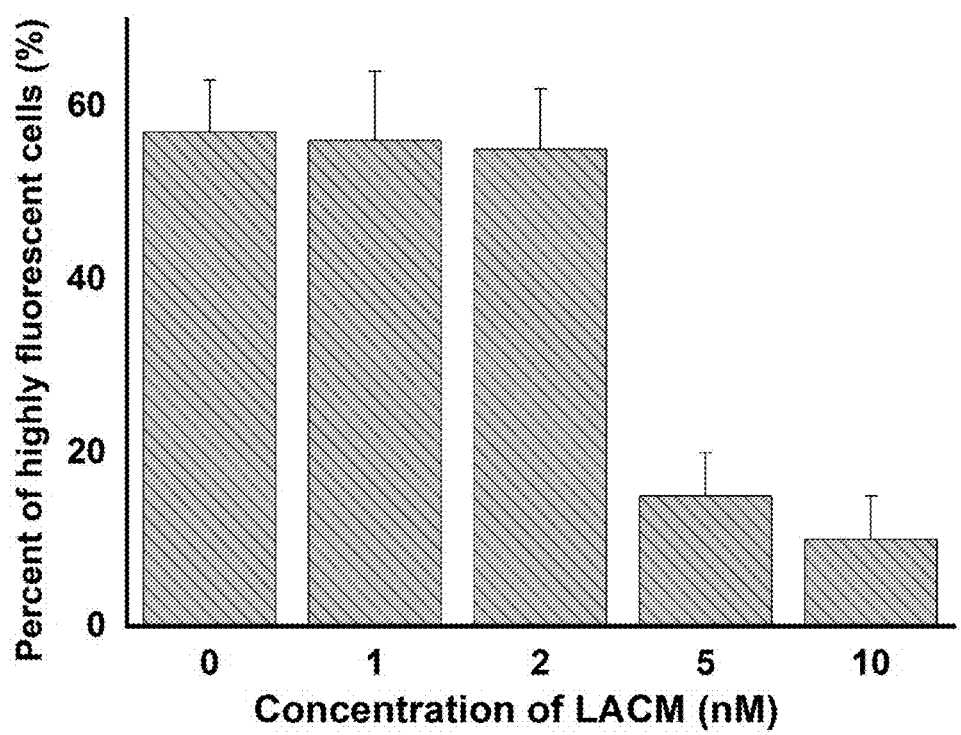
FIG. 19. Effect of incubation concentration of LACM on editing of the EGFP gene in A549 cells. A549-GFP/Cas9 cells stably expressing GFP and Cas9 proteins were used in this experiment. The cells were incubated with varying concentrations of LACM for 10 h. After cell growing for 5 days, the cells were washed, trypsinized, pelleted, and re-suspended in PBS buffer containing 2% FBS. Flow cytometry was used to analyze fluorescent cells. Highly fluorescent cells represent those containing GFP proteins. Decreases in percentage of highly fluorescent cells indicate successful editing of the EGFP gene in the cells, resulting in decreases in expression of GFP protein. Error bars represent one standard deviation from triplicate cell incubation/treatment experiments (n=3).
Figure 20:
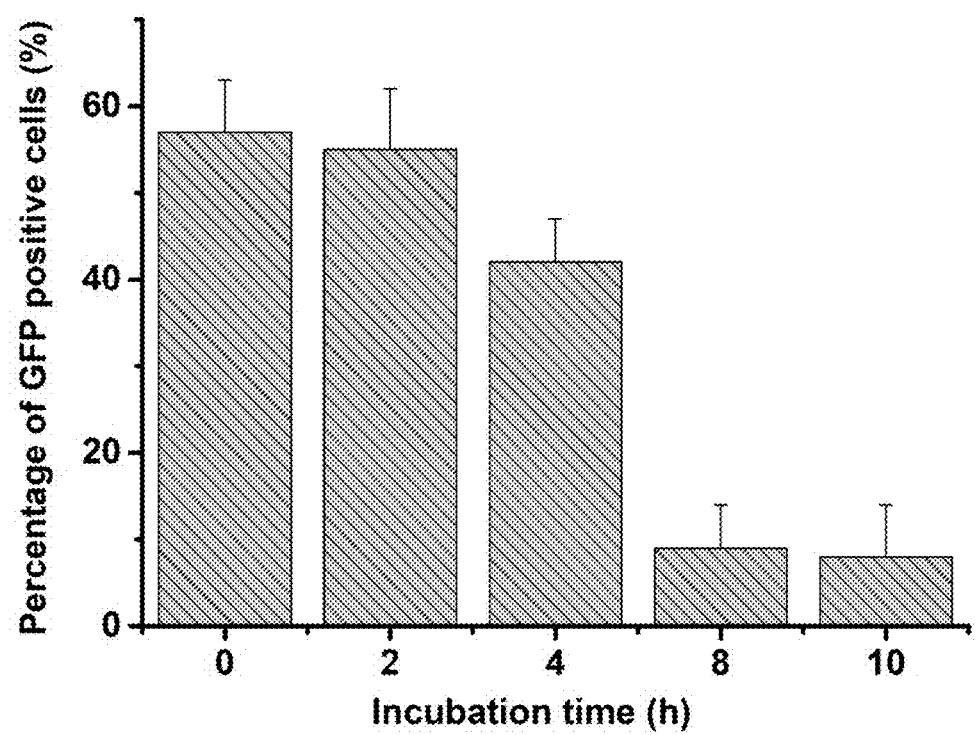
FIG. 20. Effect of incubation time of LACM on editing of the EGFP gene in A549 cells. A549-GFP/Cas9 cells stably expressing GFP and Cas9 proteins were used in this experiment. The cells were treated with 5 nM LACM for varying durations of incubation time. After cell growing for 5 days, the cells were washed, trypsinized, pelleted, and re-suspended in PBS buffer containing 2% FBS. Flow cytometry was used to analyze fluorescent cells. Highly fluorescent cells represent those containing GFP proteins. Decreases in percentage of highly fluorescent cells indicate successful editing of the EGFP gene in the cells, resulting in decreases in expression of GFP protein. Error bars represent one standard deviation from triplicate cell incubation/treatment experiments (n=3).

Editing of the EGFP and EMX1 genes in A549 cells using LACM. We used LACM to perform NIR-activated editing of the EGFP gene in A549-GFP/Cas9 cells stably expressing GFP and Cas9 proteins. Irradiation with a NIR laser (808 nm) for 10 min did not significantly affect the cell viability (FIG. 17) and was sufficient to activate the editing of EGFP in A549 cells (FIG. 18-20).

Figures 4A, 4B:
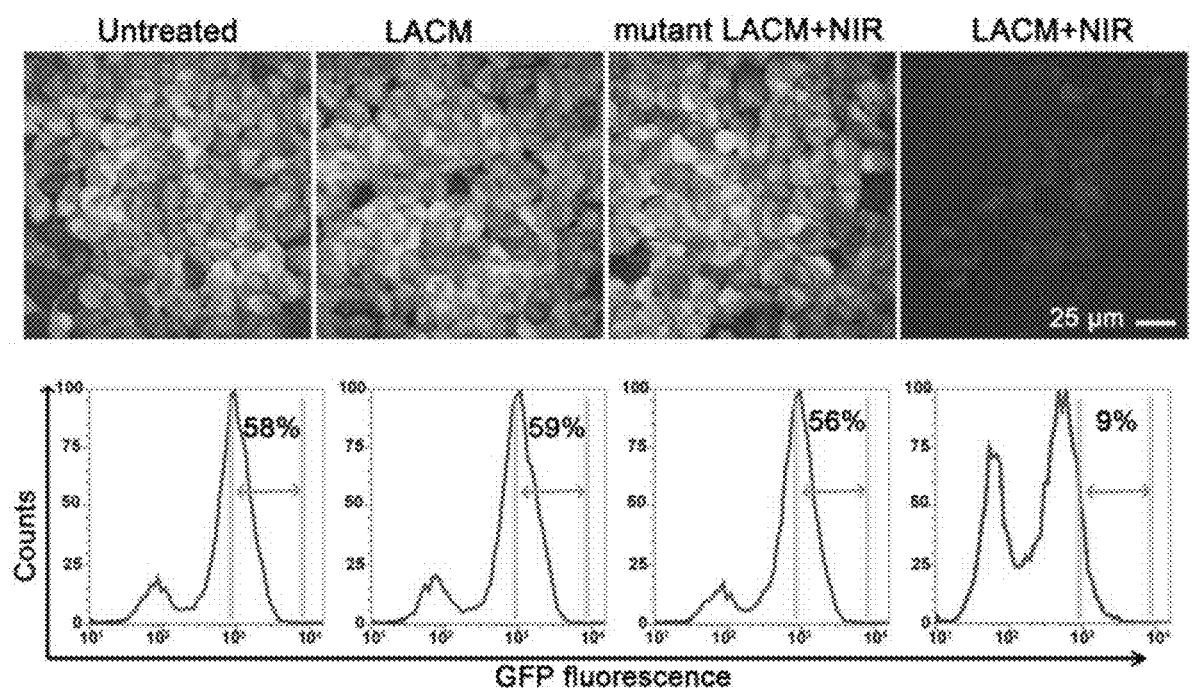
FIGS. 4A and 4B. LACM for editing EGFP in live cells.

FIG. 4a shows that the untreated A549-GFP/Cas9 cells are highly fluorescent as expected because GFP protein is highly expressed in these cells. Incubation of A549-GFP/Cas9 cells with LACM followed by NIR irradiation resulted in substantial fluorescence decreases, indicative of successful editing of the EGFP gene. Cells incubated with LACM, but not with NIR irradiation, show no decrease in fluorescence. These results demonstrate that editing of the EGFP gene can be controlled using LACM and activated by NIR irradiation. To confirm that the control of gene editing is specific for the sgRNA built into LACM, we tested a mutant LACM. The mutant LACM differed by only 2 nt (from G to A) in the target-binding domain of the sgRNA (Table 1). Results showing no fluorescence decrease (FIG. 4a, FIGS. 21 and 22) confirmed no editing of the EGFP gene by the mutant LACM.

Flow cytometry analyses (FIG. 4b, FIGS. 23-25) of A549-GFP/Cas9 cells with different treatments showed similar results to those obtained with fluorescence microscopy. Incubation of A549-GFP/Cas9 cells with LACM and irradiation with 808-nm NIR laser resulted in a substantial reduction of highly fluorescent cells, from 58% to 9%. Cells incubated with LACM, but not with NIR irradiation, or cells incubated with the mutant LACM and irradiated with NIR remained as highly fluorescent. These results support the controlled editing of the EGFP gene using LACM and NIR activation.

Figure 5A:
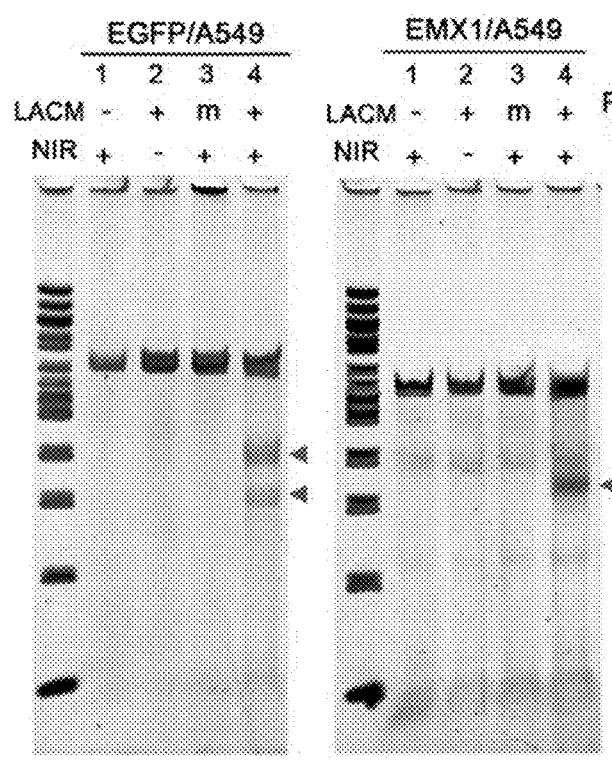
FIGS. 5A and 5B. T7E1 assay for editing EGFP and EMX1 in A549-GFP/Cas9 and HEK293T-GFP cells.

We also detected insertions and deletions (indels) mutation frequency using the T7 endonuclease 1 (T7E1) assay. Results (FIG. 5a, left-side panel) are consistent with those of fluorescence microscopy and flow cytometry (FIG. 4). The cells with LACM treatment and NIR irradiation showed 15% EGFP indel mutation, whereas no mutation was detected in the other two controls.

Figure 26:
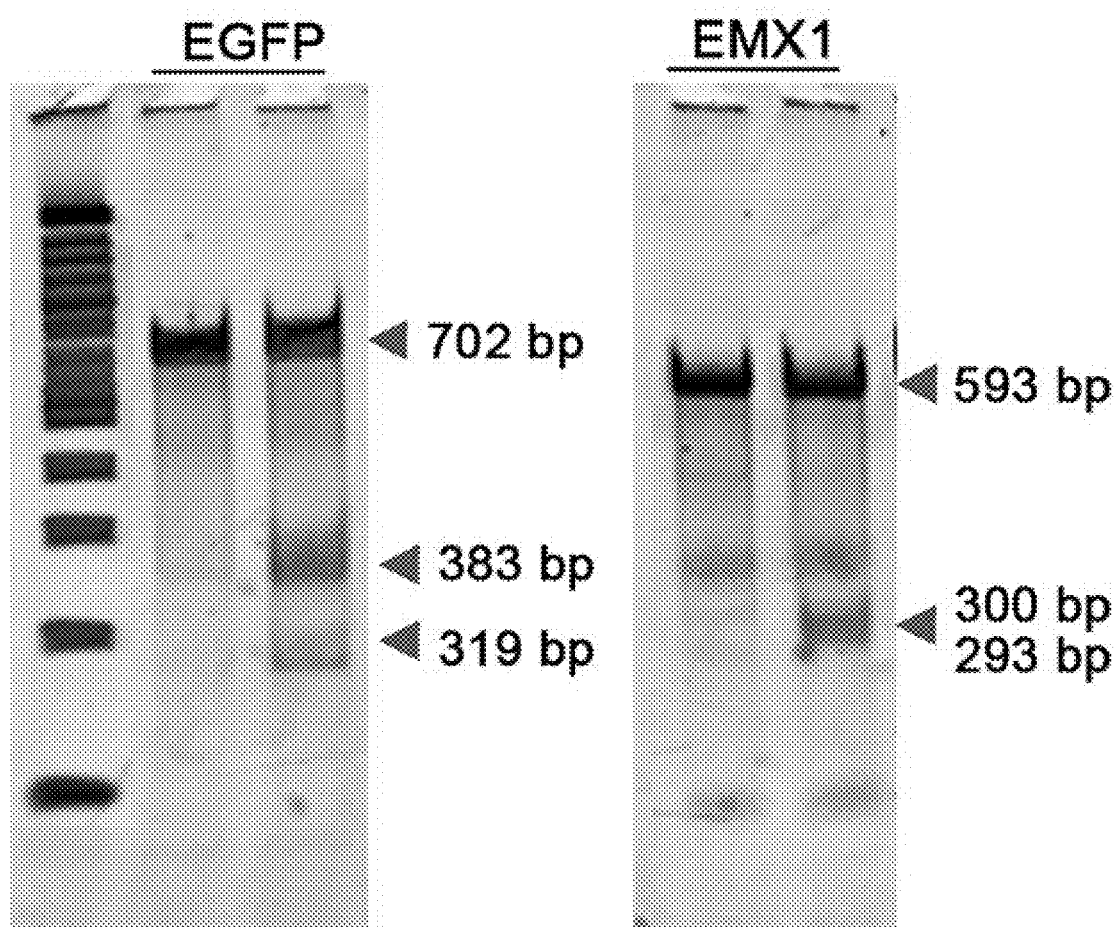
FIG. 26. Gel image showing results from the T7E1 mutation assay of A549 cells after editing of the EGFP or EMX1 gene. The cells were either not treated (left) or treated with CRISPRMAX (right), a commercially available lipofectamine transfection reagent kit. The arrows indicate the unmodified gene and the cleavage products. T7E1 assay showed that the indel of gene mutation frequency for the EGFP gene was 17% in the treated cells, and 0% in the untreated cells. The indel of gene mutation frequency for the EMX1 gene was 13% in the treated cells, and 0% in the untreated cells.

We further compared the gene editing efficiency of LACM with that of the standard Lipofectamine transfection method. T7E1 assay show similar indel frequency achieved with LACM and with the established Lipofectamine transfection method (FIG. 26). As compared to the Lipofectamine transfection of Cas9 ribonucleoprotein, our LACM technique has two advantages: controllable and no need for transfection reagent.

To test the general applicability of LACM for editing other genes, we constructed a LACM targeting human EMX1. The EMX1 gene is implicated in embryonic brain development. The construction of the LACM for editing EMX1 was achieved by simply altering the sequence of the target-binding domain in sgRNA and the sequence of the protector. T7E1 assay (FIG. 5b, right-side panel) show that the indel frequency was 10%, representing successful gene editing. The control treatment did not have gene editing response. These results show that the LACM technique is applicable to controlled editing of different genes.

Figure 29:
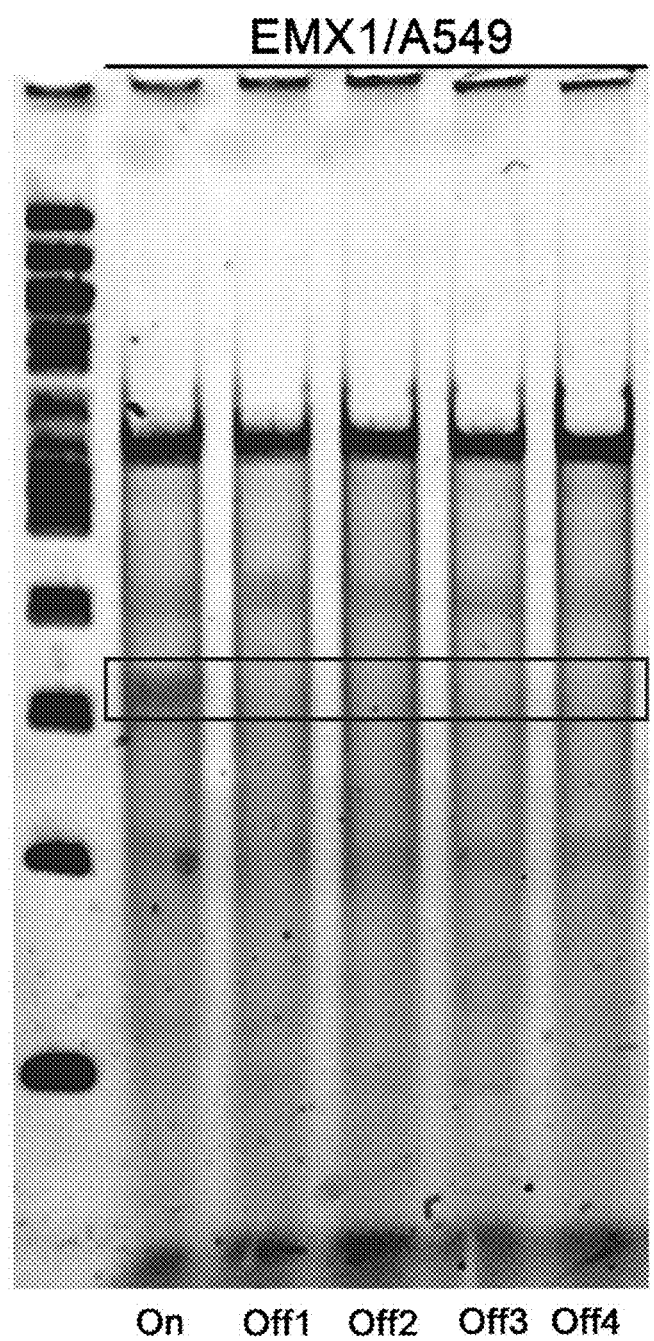
FIG. 29. Gel image from the T7E1 assay showing editing of the EMX1 gene and no editing to its four known off-target genomic sites. The target sequences of EMX1 and its four known off-target genomic sites are listed below. Mutation sites are labeled in lower-case letters and in red color.

We determined the specificity of gene editing by monitoring the on-target and four well-known off-target genomic sites of the EMX1 gene.[39] These four off-target sites contain 2 or 3 different nucleotides compared to the editing sequence of EMX1.[37] Previous studies have shown high probability of off-target editing from these four sites.[40-42] Our results of the T7E1 assay show an expected 10% indel frequency for the on-target editing of the EMX1 sequence and no observable gene editing of the other four off-target sites (FIG. 29). These results demonstrate that gene editing using the LACM strategy is specific for the target editing.

Editing of the EGFP and EMX1 Genes in HEK293T Cells Using LACM.

Figure 5B:
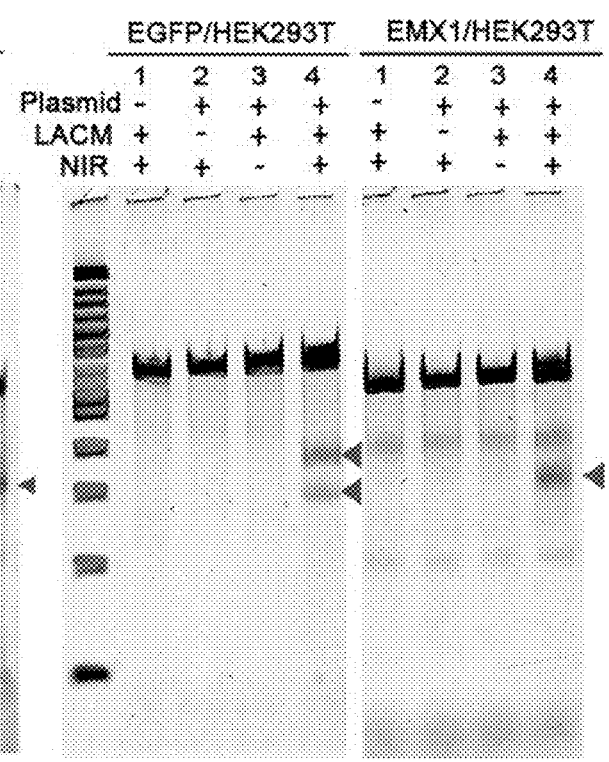

We extended LACM for editing EGFP and EMX1 in HEK293T-GFP cells (FIG. 5b). This cell line does not have stable expression of Cas9. Thus, we transfected the cells with the Cas9 plasmid using lipofectamine 12 h prior to the treatment with LACM. T7E1 assay shows successful editing of EGFP and EMX1 in HEK293T cells, achieving 9% and 6% indel mutation frequency, respectively.

Editing of the Polo-Like Kinase-1 (PLK1) Gene to Induce Apoptosis of Cancer Cells.

We further applied LACM to the editing of the PLK1 gene and examined the ability of LACM to kill cancer cells in a controlled manner. As a pro-oncogene functioning in mitotic progression, PLK1 is over expressed in a number of cancer cells, including A549 lung cancer cells.[43] The PLK1 gene has been studied as a target for cancer therapy, and silencing of PLK1 can cause apoptosis of cancer cells.[44,45] We constructed a LACM incorporating a sgRNA that targets the PLK1 gene, and used this LACM to edit PLK1 in A549 cells, thereby inducing apoptosis of cancer cells.

Figure 6A:
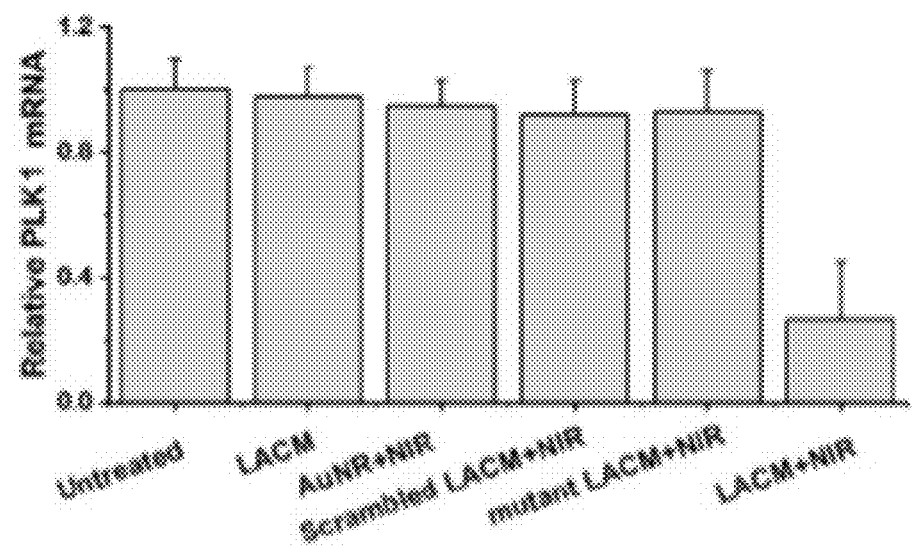
FIGS. 6A-6C. Analysis of mRNA and protein levels of PLK1 as well as apoptosis in A549 lung cancer cells treated with LACM or five controls.
Figure 6B:
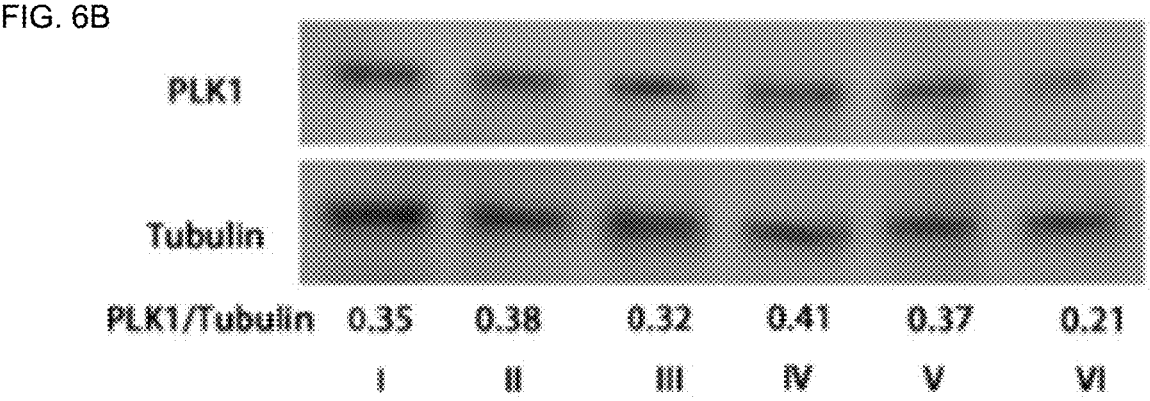

We determined the level of PLK1 messenger RNA (mRNA) using reverse transcription quantitative PCR (FIG. 6a), and the PLK1 protein level using Western blotting (FIG. 6b). After two-day treatment, the level of PLK1 mRNA was reduced by about 70% in cells subjected to LACM treatment and NIR irradiation. There is no significant decrease in the mRNA level in control cells, including those treated with LACM but no NIR irradiation, cells treated with LACM containing a mutant sgRNA, cells treated with LACM containing a scrambled sgRNA sequence, or cells treated with AuNR not functionalized with sgRNA. Consistent with the results of mRNA, a significant decrease in the level of the PLK1 protein (FIG. 6b) is observed only in cells treated with LACM followed by NIR irradiation. There is no significant decrease in the level of PLK1 protein in any of the control cells. Results from the immunostaining of the cells with the antibody against PLK1 also confirm a lower level of the PLK1 protein in the cells treated with LACM followed by NIR irradiation (FIG. 30).

Figure 6C:
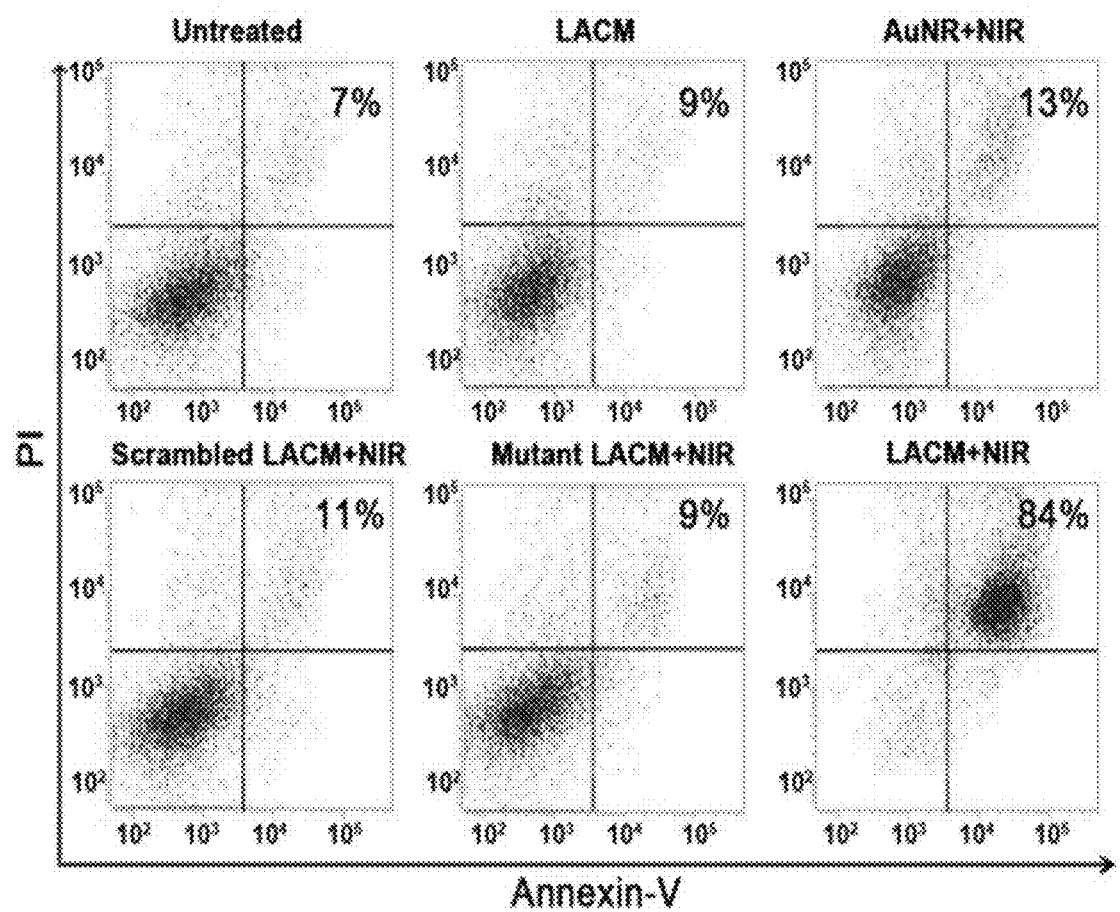

We then examined knock down of PLK1 expression and the consequent induction of apoptosis of cancer cells. Flow cytometry analyses of the treated cells show increases in apoptotic cells from less than 10% (control) to 84% after the cells were treated with LACM and irradiated with NIR laser (FIG. 6c). There is no significant increase of apoptosis in the four control groups. These results indicate that LACM is capable of knocking down the expression of the PLK1 gene and inducing apoptosis of the cancer cells.

CONCLUSION

Our results from the flow cytometry, microscopy, T7E1 assays, RT-qPCR, and immunoblotting have consistently demonstrated the laser-activated control of sgRNA for editing two genes (EGFP and EMX1) in two cell lines (A549 and HEK293T) and for knocking down the PLK1 gene to induce apoptosis of cancer cells. Our LACM strategy incorporates nucleic acid assembly on AuNRs, achieving the benefits of efficient cellular uptake and inducible thermal effects by a NIR laser. The design of the protector assembly enables sequestering of the sgRNA to an inactive form and efficient release by NIR laser activation. Application of a NIR laser (808 nm) to activate the release of sgRNA for gene editing is advantageous for future applications because the NIR wavelength is known to penetrate tissues with spatial-temporal precision and minimal invasiveness. The LACM strategy possesses several appealing features that can be readily integrated into a variety of CRISPR-associated techniques and applications, such as genome editing, transcriptional perturbation, epigenetic modulation, genome imaging, and gene therapy.

Methods

Materials. 10×40-nm gold nanorod (AuNR) was obtained from Nanopartz Inc. (Loveland, CO, USA). PLK-1 monoclonal antibody (#35-206), horse radish peroxidase (HRP)-labeled goat anti-mouse IgG (H+L) cross-adsorbed secondary antibody (#G-21040), goat anti-mouse IgG (H+L) cross-adsorbed secondary antibody with Alexa Fluor 546 (#A-11003), RIPA lysis buffer, Lipofectamine™ CRISPRMAX™, Lipofectamine 2000, TRIzol reagents (#15596026), SYBR® Green Real-Time PCR master mix reagents kit, SuperSignal™ West Pico Plus chemiluminescent substrate kit, and LIVE/DEAD® viability/cytotoxicity kit were purchased from ThermoFisher Scientific (New Hampshire, USA). Annexin V-PI-FITC Apoptosis Detection Kit was obtained from BioVision Inc. (Milpitas, USA). BCA protein assay kit and monoclonal anti-β tubulin antibody (#T5201) were obtained from Sigma-Aldrich (St Louis, MO, USA). QIAquick gel extraction kit and QIAquick PCR purification kit were purchased from QIAGEN (Germany). Q5® high-fidelity DNA polymerase, EnGen™ Spy Cas9 NLS nuclease and T7E1 enzyme were obtained from New England Biolabs (USA).

Production and Purification of sgRNA.

The DNA template of sgRNA was produced using a fill-in PCR. Briefly, PCR was performed using two long primers: (1) a 65-nt customized forward primer containing the T7 promoter (TAATACGACTCACTATA)(SEQ ID NO: 51) and the 20-nt sgRNA DNA-targeting sequence; (2) an 80-nt reverse primer encoding the 3' tail sequence of sgRNA. Two primers have a 20-nt complementary sequence. PCR was carried out in a thermal cycler with the following thermal cycling program: 95° C. for 2 min; 35 cycles of 95° C. for 20 s, 60° C. for 30 s, and 72° C. for 15 s; and a final step of 72° C. for 10 min. The PCR product (125-bp) was purified using San Prep Column PCR Product Purification Kit and was used as a template for a T7 RNA polymerase-mediated transcription reaction. The sg RNA transcription reaction was performed with purified DNA template at 37° C. overnight, and the product was purified using RNAclean Kit (Tiangen). The purified sgRNA was stored at −80° C. for subsequent use.

Construction of the CRISPR/Cas9 Nano-Machine (LACM) Photothermally Activated Using a NIR-Laser.

Figure 7C:
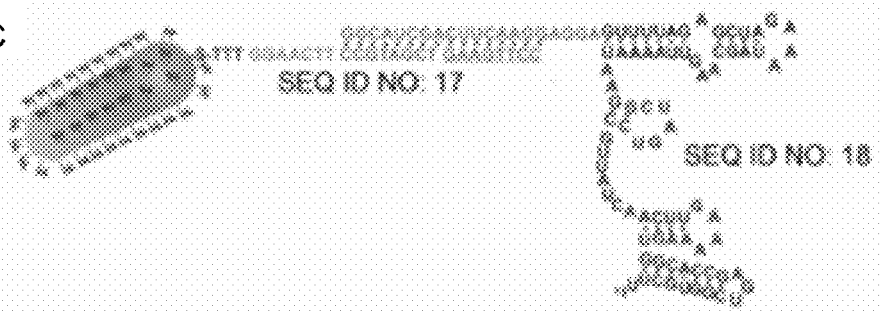
Figure 7D:
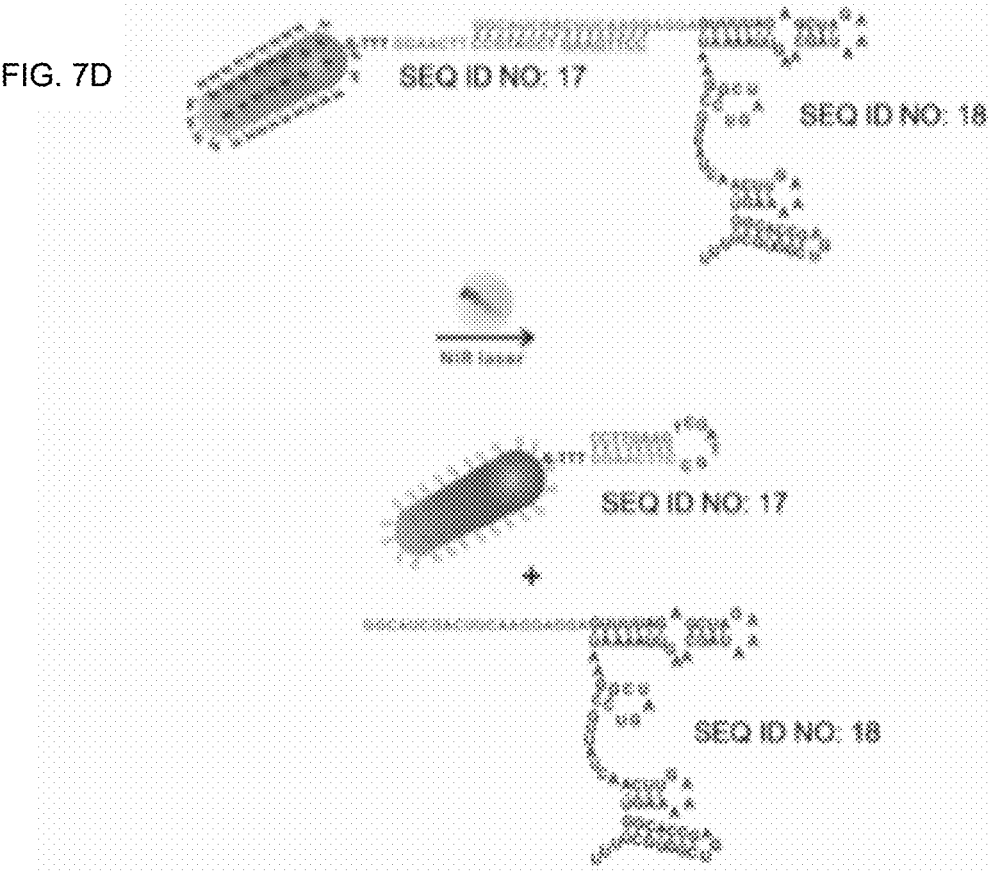

The LACM was constructed using a 10×40-nm gold nanorod (AuNR) as the carrier that was functionalized with dozens of protected sgRNA strands.[46] The sequences of the sgRNA and protector strand are summarized in Table 1 and FIG. 7, with complementary sequences showing in identical matching colors. The 3'-end of the protector strand that was conjugated to AuNRs was thiolated. Prior to conjugation to the AuNRs, the sgRNA was protected by the protector strand through hybridization between the sgRNA and the protector strand. The protector strand and the sgRNA strand were mixed at a molar ratio of 1:2 in 100 mM NaCl and 10 mM Tris-HCl (pH 7.4) buffer. The two-fold molar excess of the sgRNA strand was used to ensure that all protector strand was hybridized with sgRNA. The mixture was heated to 85° C. for 5 min and then slowly cooled to 4° C. at a rate of 1.2° C./min.

The protected sgRNA was conjugated to AuNR using the following procedures. The thiolated 3'-end of the protector was reduced using TCEP. The duplex of the sgRNA and the protector oligo was mixed with AuNR at a molar ratio of 1000:1. The solution was first incubated at room temperature for half an hour. Tween 80 (4%) was then added to make the final solution contain 2% Tween 80, which was used to reduce adsorption and aggregation of AuNRs. A solution of 5 M NaCl was added to make a final concentration of 2 M NaCl. The solution was sonicated for 1 min every 30 min. After incubation at room temperature for 3 h, the solution was centrifuged at 16,000 g for 10 min to separate the AuNRs from the unconjugated oligonucleotides. The AuNRs were collected and washed four times using 1 mL of 10 mM Tris-HCl containing 0.05% Tween 20 and 100 mM NaCl. The AuNRs were re-suspended in 10 mM Tris-HCl buffer containing 100 mM NaCl. A typical concentration of the decorated AuNRs was 10 nM. The solution was stored at 4° C. until use.

Examination of the Protection Efficiency of the sgRNA Strand.

Figure 8:
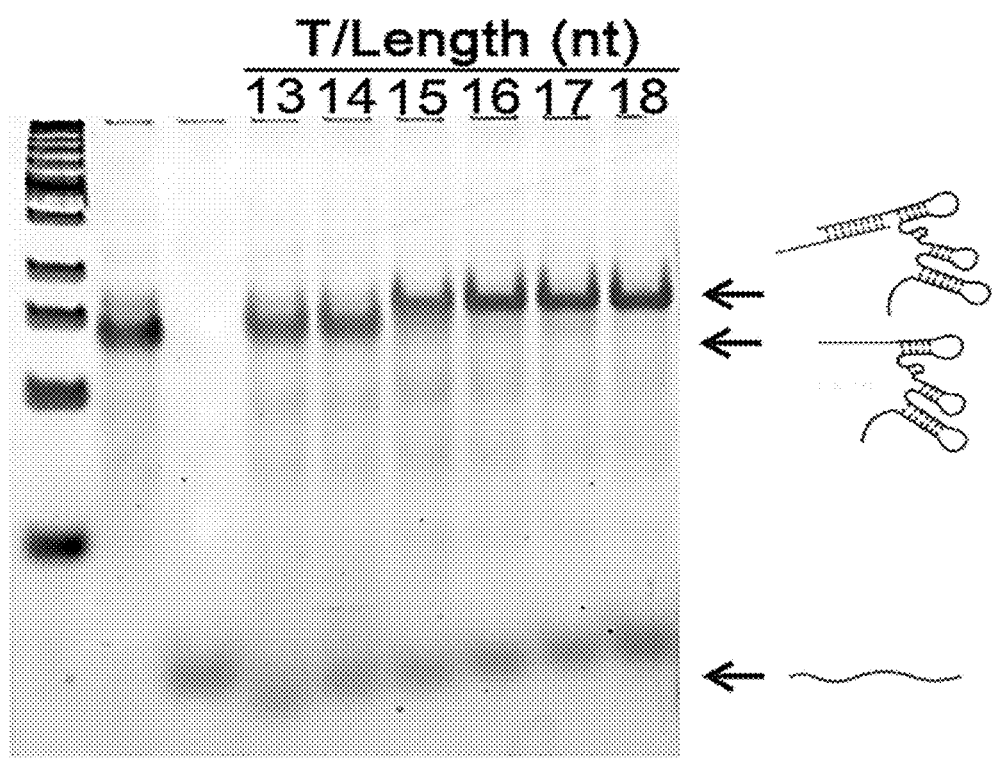
FIG. 8. Gel electrophoresis images showing formation of a duplex between the sgRNA and protectors containing different lengths of target-binding domain (T). From left to right Lane 1 to Lane 9. Lane 1: DNA ladder; lane 2: sgRNA; lane 3: protector DNA; lanes 4-9: mixture of sgRNA and protector with target-binding domain length from 13 to 18 nt. This set of experiments was designed to examine the efficiency of hybridizing sgRNA to six protectors containing the target-sequestering domain (T) of 13, 14, 15, 16, 17, or 18-nt (Table 1). Each protector was mixed with sgRNA at a 1.5 to 1 molar ratio. The solution was heated to 85° C. for 5 min and then slowly cooled down to 20° C. within 1 h to allow for annealing. Gel electrophoresis analyses show that when the T domain is longer than 15 nt, sgRNA is completely hybridized to the protector DNA and there is no detectable free sgRNA. With a molar ratio of greater than 1.5 between the protector and the sgRNA, the sgRNA is completely hybridized to the protector.

Hybridization of the sgRNA to the protector strand was examined using native polyacrylamide gel electrophoresis (PAGE) (FIGS. 8 and 9). Specifically, 4 µL of 1 µM sgRNA was mixed with 4 µL of 1 µM protector strand, followed by an addition of 2 µL of 100 mM Tris-HCl and 1 M NaCl buffer (pH 7.2). The solution was then diluted to a total volume of 20 µL. To facilitate the hybridization of sgRNA by the protector strand, the mixture was heated to 85° C. for 5 min and then slowly cooled down to 4° C. at a rate of 1.2° C./min using a Bio-Rad thermal cycler (Bio-Rad, Hercules, CA). 8% polyacrylamide gel was used to separate the hybridized duplex from the free sgRNA and protector strand. Gel electrophoresis was carried out at 100 V for 40 min. The gel was stained with SYBR® Gold for 15 min and imaged using ImageQuant LAS 4000.

Determination of the Number of sgRNA Molecules Assembled on AuNRs.

A single-stranded oligonucleotide, with the sequence complementary to the 5'-end of the sgRNA, was labeled with FAM at its free 3'-end. This FAM-labeled oligonucleotide was hybridized to the protected sgRNA, forming a ternary complex. This ternary complex was then conjugated to AuNRs (FIG. S5, FAM-modified $T_{16}S_8$-LACM).

For the determination of average number of sgRNA molecules assembled on each AuNR, 2-mercaptoethanol was used to release the conjugated ternary complex from the AuNRs. The fluorescence of the released complex was determined and used to derive the average number of the sgRNA molecules on AuNR. Specifically, 10 µL of 1.1 nM AuNR solution was mixed with 10 µL of 35 mM 2-mercaptoethanol. The mixture was diluted to 100 µL with 1×PBS buffer. After an overnight incubation at room temperature, the solution was centrifuged at 16,000 g for 10 min. A 95-µL supernatant was transferred onto a 96-well plate (Fisher Scientific, Ottawa, ON), which was then loaded onto a fluorescence microplate reader (Beckman Coulter, DTX 800) for fluorescence detection. Molar concentrations of the sgRNA were determined against a calibration of the FAM-labeled oligonucleotide. Our results showed that on average, 60 protected sgRNA strands were assembled on each AuNR. With a surface area of 1570 nm$^2$ of a 10×40 nm AuNR, the densities of the protected sgRNA strands are 3.8×10$^{-2}$/nm$^2$ on the AuNRs.

Assay for Cleavage of Double-Stranded DNA Substrate of CRISPR/Cas9.

Double-stranded DNA (dsDNA) substrates were used to test the cleavage activity of a CRISPR/Cas9 system. The dsDNA substrate was first generated by amplifying the targeted EGFP locus or EMX1 locus from genomic DNA using MJ Mini™ Thermal Cycler. The prepared dsDNA substrate was characterized using 4% polyacrylamide gel stained with SYBR® Gold (Invitrogen), and quantified using a NanoVue Plus. The CRISPR/Cas9 cleavage assay was performed using the following procedures. 100 nM Cas9 nuclease (New England Biolabs, USA) was first incubated with 100 nM sgRNA in the reaction buffer (20 mM HEPES, 100 mM NaCl, 5 mM MgCl$_2$, 0.1 mM EDTA, pH 6.5) having a total volume of 27 µL. After incubation of the mixture at 25° C. for 10 min, 3 µL of 100 nM dsDNA substrate was added, followed by incubation at 37° C. for 1 h. The reaction was then stopped by heating at 95° C. for 5 min. 4% polyacrylamide gel was used to separate the dsDNA substrate (702 bp) from the cleaved products (319 bp and 383 bp) (FIG. S6). Gel electrophoresis was carried out at 100 V for 40 min. The gel was stained with SYBR® Gold for 15 min and imaged using a fluorescence gel imaging system (ImageQuant LAS 4000, GE Healthcare Life Sciences, Pittsburgh, PA).

Evaluation of the Activation of LACM Using a NIR Laser.

An 808 nm laser (Sunshine-electronics INC, USA) with a 2 W power was employed for irradiation. The irradiation area was magnified to 1 cm$^2$ using an optical lens. The temperature of the solution was monitored in real time using a FLIR thermal camera. 2.5 nM of LACM was first irradiated using the 808 nm laser for 1 min, and then incubated with 100 nM Cas9 protein for 10 min at 37° C. 10 nM dsDNA substrate was then added into the mixture to initiate the substrate cleavage. After 1 h reaction, the mixture was heated to 95° C., and analyzed using 4% polyacrylamide gel.

Examination of the Release Efficiency of the sgRNA Strand after NIR Irradiation.

The release efficiency of the sgRNA strand was examined using the dsDNA substrate cleavage assay. 2.5 nM of LACM was subjected to NIR irradiation for different times to release sgRNA from AuNR. The released sgRNA was then incubated with 100 nM Cas9 protein at 37° C. for 10 min, followed by an addition of 10 nM dsDNA substrate into the mixture. The cleaved substrates were analyzed using 4% native PAGE. The cleavage percentage was normalized to the cleavage efficiency obtained using 100 nM free sgRNA. Complete release of the protected sgRNA was achieved after 30 second irradiation of LACM in solution.

Examination of the Cellular Uptake of the LACM.

The cellular uptake of LACM was determined using inductively coupled plasma mass spectrometry (ICP-MS) and confocal fluorescence microscopy.

Forty thousand (40,000) cells per well were seeded onto a 24-well plate. When cultured to 80-90% confluence, cells were washed with 1×PBS for three times. To each well was added 200 µL of the Opti-MEM Reduced Serum Medium (Fisher Scientific, Ottawa, ON) supplemented with different concentrations of LACM. After incubation for 2, 5, 8, and 10 hours, cells were thoroughly washed with 1×PBS for six times. Cells were then detached using 0.05% trypsin-EDTA and collected using centrifugation. The number of cells was counted using a hemocytometer. Collected cells were lysed and digested with 10% ultrapure nitric acid at 60° C. overnight. The amount of AuNRs was measured by detecting Au at m/z 197 using ICP-MS (Agilent 7500cs, Japan), against a calibration of acid-digested AuNR standards. The uptake number of AuNRs per cell was then derived from the total amount of AuNRs and cell number. Based on the results of cell imaging, the cell size of 20 µm diameter was used to estimate the intracellular AuNR concentrations.

Cellular uptake of LACM was determined using confocal fluorescence microscopy. The protected sgRNA was hybridized with a FAM-labeled oligonucleotide at its free 3'-end, forming a ternary complex. This ternary complex was used to construct LACM (FIG. 11, FAM-modified $T_{16}S_8$-LACM). Fluorescence imaging of live cells was acquired using an Olympus IX-81 microscope that is coupled with a Yokagawa CSUx1 spinning disk confocal scan-head and Hamamatsu EMCCD camera with 20×/0.85 Oil objective lenses. Two pumped diode lasers with wavelengths of 491 nm and 358 nm were used for the excitation of FAM and DAPI, respectively. The exposure time was set to be 180 ms for FAM and 200 ms for DAPI.

Cell Viability Assay.

Cell viability was assessed using the LIVE/DEAD® Viability/Cytotoxicity Kit. Briefly, an aliquot of 10 µL of the reagent of the LIVE/DEAD® kit was added to the cells, mixed gently, and incubated on ice for 30 min. The fluorescence intensity of cells was then analyzed using flow cytometry. The cells with low fluorescence intensity, measured using 405 nm excitation and ~525 nm emission, represented the number of live cells.

Flow Cytometry Analysis.

Cells were cultured at 37° C. and 5% CO$_2$ in a humidified incubator. A549-GFP/Cas9 (GFP-Puro) cells (GenTarget Inc, USA) was grown and maintained in RPMI 1640 medium (Invitrogen) supplemented with 10% fetal bovine serum (FBS, Invitrogen), penicillin/streptomycin (pen/strep, Invitrogen) and 1 µg/mL puromycin.

Twenty thousand (20,000) cells per well were seeded in a 96-well plate. When cultured to 80-90% confluence, cells were washed with 1×PBS twice. The cells were incubated for 10 h with Opti-MEM reduced serum medium supplemented with the desired concentrations of LACM, to allow for the cellular uptake of LACM. Cells were then washed with 1×PBS twice and with Opti-MEM reduced serum medium for another two times. Opti-MEM reduced serum medium was added to the cells, and cells were irradiated with the 808-nm laser for 10 min. Cell medium was replaced with the growth medium (RPMI 1640 medium supplemented with 10% fetal bovine serum, penicillin/streptomycin and 1 µg/mL puromycin). After a growth period of 5 days, the cells were washed with 1×PBS and then detached using 0.05% trypsin-EDTA. The cell pellet was then re-suspended in 200 µL 1×PBS with 2% FBS. LIVE/DEAD® Viability dye was added following the instructions of the kit. After 30 min incubation, the cell sample was analyzed using flow cytometry.

Figure 21:
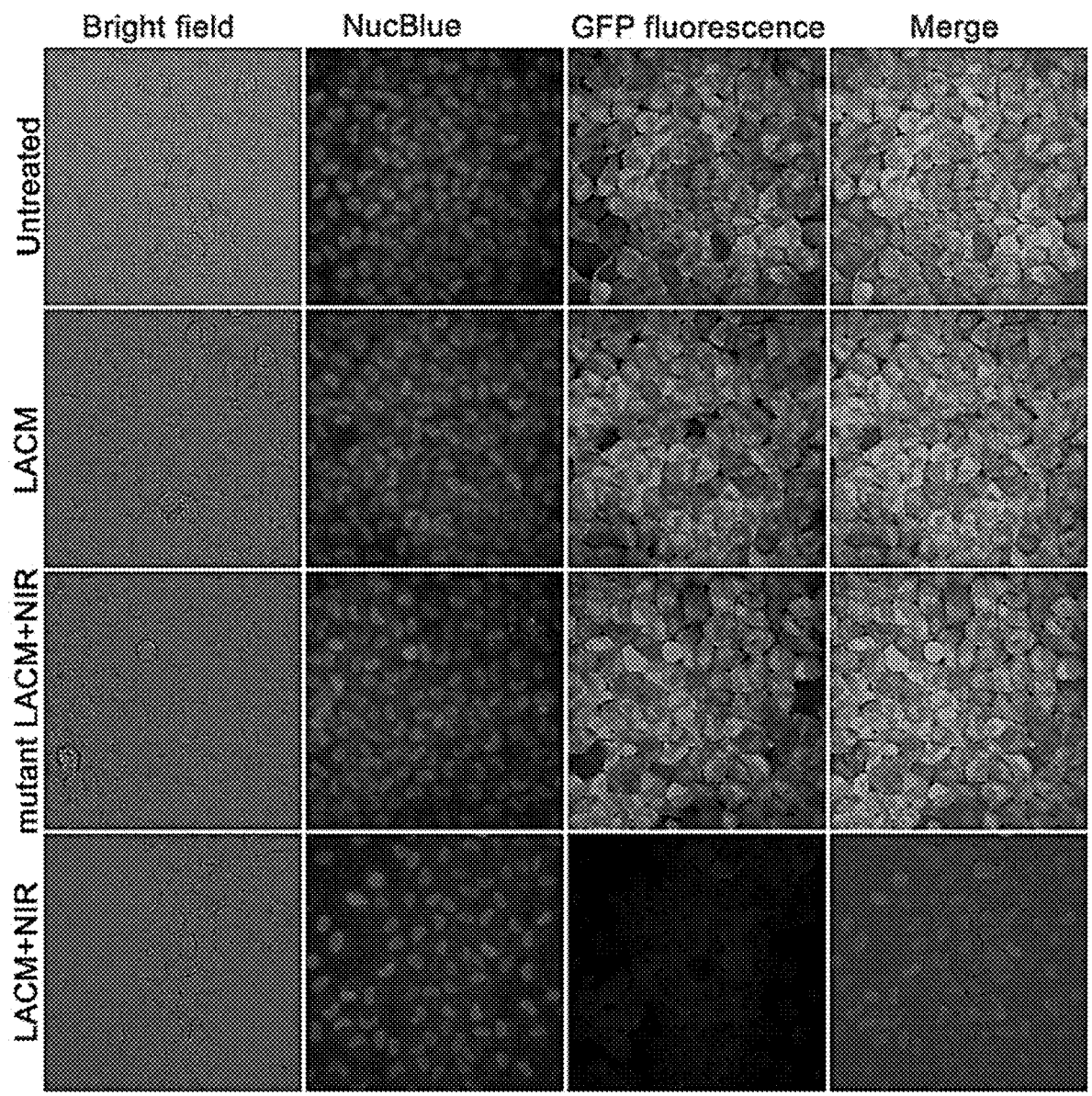
FIG. 21. Confocal images of A549-GFP/Cas9 cells stably expressing GFP and Cas9 proteins. From top to bottom: untreated cells, cells treated with LACM but no NIR irradiation, cells treated with mutant LACM and with NIR irradiation, and cells treated with LACM and with NIR irradiation (808 nm). NucBlue stains nucleus of the cells. Green fluorescence protein (GFP) is highly expressed in the A549-GFP/Cas9 cells.
Figure 22:
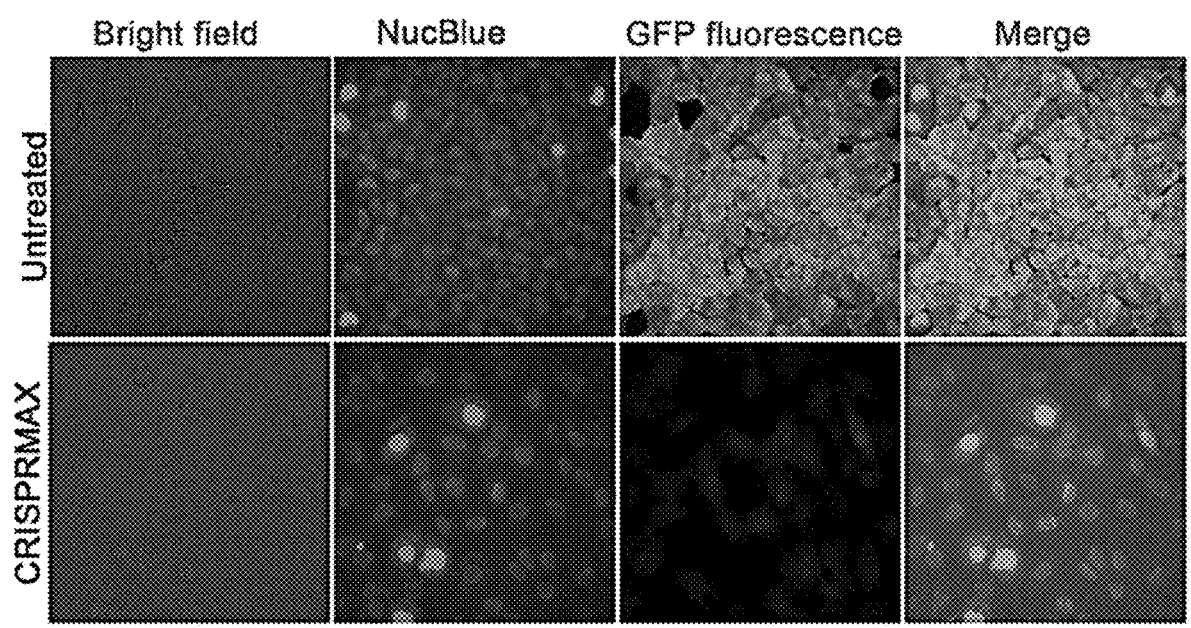
FIG. 22. Confocal images of A549-GFP/Cas9 cells stably expressing GFP and Cas9 proteins. Images on the top were from the untreated cells (Control). Image on the bottom were from the cells treated with a commercially available lipofectamine transfection kit (CRISPRMAX). The transfection treatment introduced sgRNA to the cells for editing the EGFP gene. Decreases in GFP fluorescence intensity indicated successful editing of EGFP in the cells.
Figure 23:
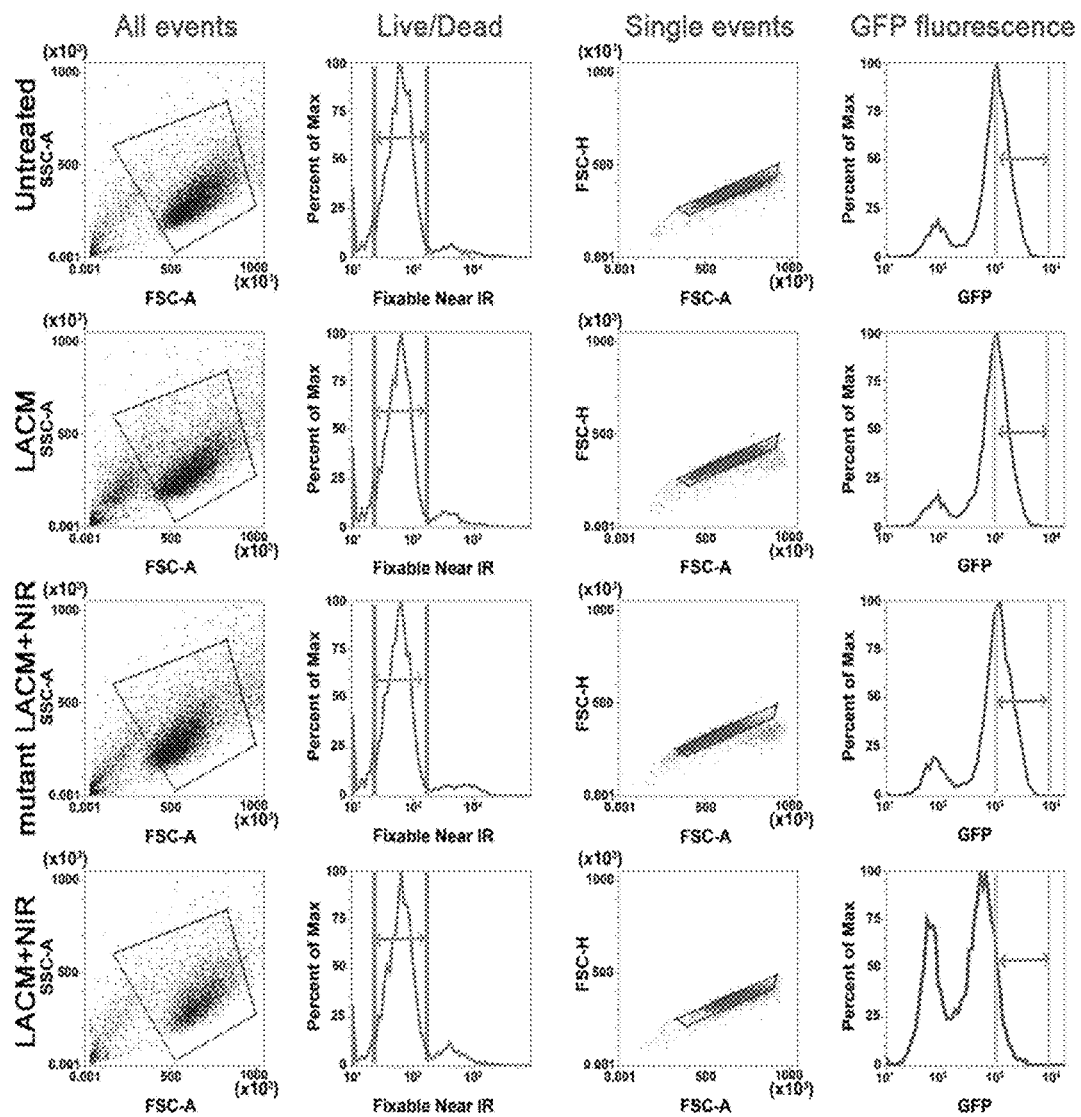
FIG. 23. Representative flow cytometry histograms of A549-GFP/Cas9 cells. From top to bottom: untreated cells, cells treated with LACM but no NIR irradiation, Cells treated with mutant LACM and with NIR irradiation, and cells treated with LACM and with NIR irradiation (808 nm), respectively. Cells with high fluorescence intensity were gated. Live/Dead stain with LIVE/DEAD® Viability/Cytotoxicity Kit showed no difference among the cells with the different treatments. The shift of GFP fluorescence to a lower intensity from the analysis of the cells treated with the LACM and irradiated with the NIR laser (808 mm) for 10 min was a result of successful editing of the EGFP gene in the cells.
Figure 24:
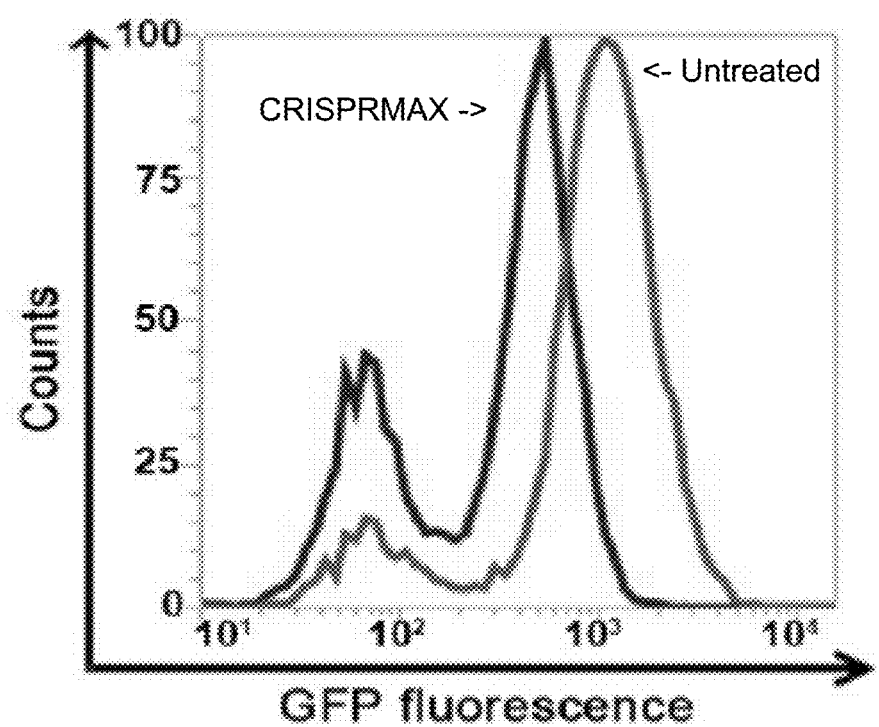
FIG. 24. Representative flow cytometry histograms of A549-GFP/Cas9 cells stably expressing GFP and Cas9 proteins. The blue trace was obtained from the analysis of untreated A549-GFP/Cas9 cells (Control). The red trace was from the analysis of the cells after treatment with a commercially available lipofectamine transfection kit (CRISPRMAX). The transfection treatment introduced sgRNA to the cells for the editing of the EGFP gene. In the cell population, shifting of the GFP fluorescence to a lower intensity was a result of editing of the EGFP gene in the cells.
Figure 25:
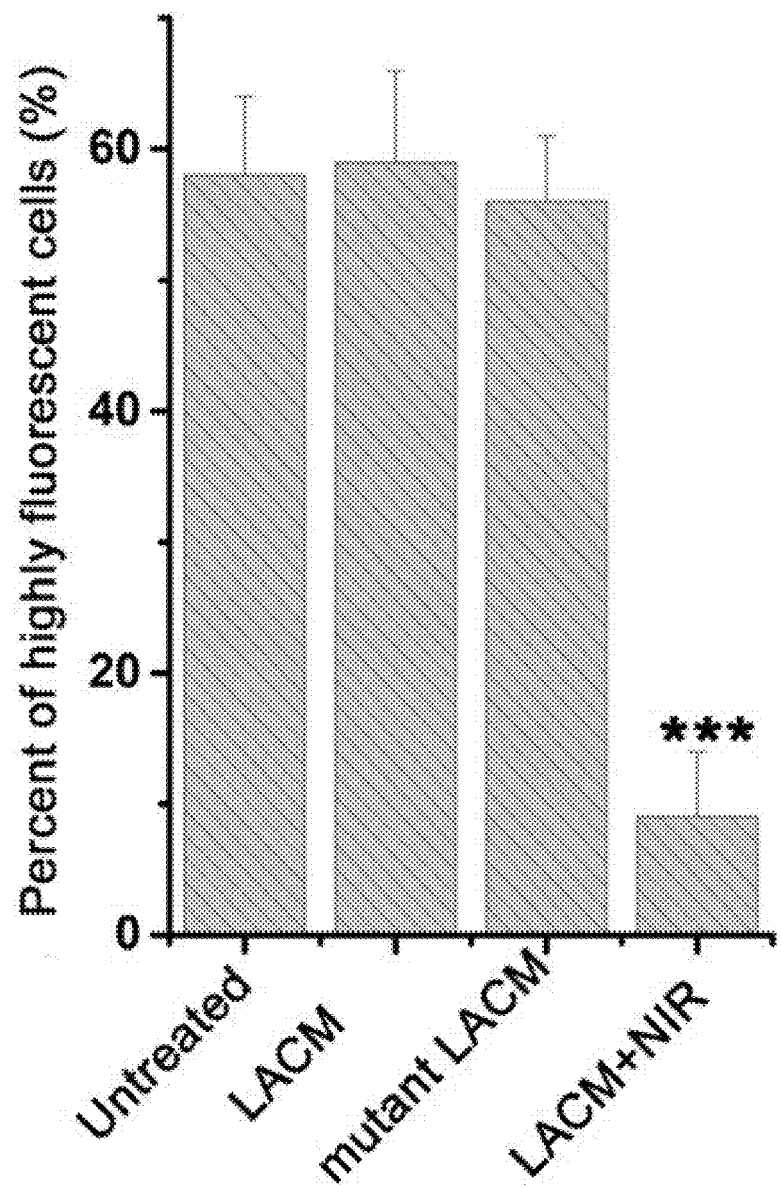
FIG. 25. Flow cytometry analyses of A549-GFP/Cas9 cells after different treatments. Incubation of A549-GFP/Cas9 cells with LACM and irradiation with 808-nm NIR laser resulted in a substantial reduction of highly fluorescent cells, from 58% to 9%. Cells incubated with LACM, but not with NIR irradiation, or cells incubated with the mutant LACM and irradiated with NIR remained as highly fluorescent. ***p<0.001 is from a t-test comparing with the untreated cells.

Editing of EGFP reduced transcription of the green fluorescence protein (GFP), leading to decreases in fluorescence of the cells. This fluorescence decrease was monitored using flow cytometry (FIGS. 23 and 25) and confocal fluorescence microscopy (FIGS. 21 and 22).

The control experiments included (1) cells without LACM treatment, (2) cells treated with LACM but without NIR laser irradiation, (3) cells treated with a mutant LACM, and (4) cells treated with a commercial kit (CRISPRMAX). The first three served as negative controls. The editing of the EGFP gene in A549/Cas9 (GFP-Puro) cells using CRISPRMAX as the transfection kit served as a positive control, and was used to compare its editing efficiency with that of the LACM system.

The T7E1 Mutation Detection Assay.

Genomic DNA was extracted using Quick Extract kit, and then diluted to 0.1 µg/mL. A DNA sequence containing the on-target site was amplified using PCR amplification. The reaction solution contained 100 ng genomic DNA, 0.5 µM primers and the Q5® Hot Start High-Fidelity 2×Master Mix. The amplification was conducted using a thermal cycling program: initial denaturation at 98° C. for 1 min, then 30 amplification cycles of 98° C. for 5 s, 67° C. for 10 s, and 72° C. for 20 s, and followed by a final extension at 72° C. for 2 min.

An aliquot of 5 µL of each amplicon was mixed with 2 µL of 10×NEB buffer and 12.5 µL H$_2$O. The amplicon was denatured and rehybridized in a thermal cycler programmed to incubate at 95° C. for 5 min and decrease to 85° C. with a 2° C./sec ramp rate, remain at 85° C. for 5 sec and decrease to 25° C. with a 0.1° C./sec ramp rate. An aliquot of 0.5 µL of 10 U/µL T7E1 enzyme (NEB M0302L) was then added and the reaction mixtures were incubated at 37° C. for 30 min. After termination of the reactions by adding 1 µL Proteinase K, half of each sample was electrophoresed on a 4% PAGE gel, stained with SYBR-Gold, and imaged using ImageQuant LAS4000. The density of bands representing the cleaved and uncleaved products were measured using ImageJ.

Evaluation of Editing the EGFP and EMX1 Genes Using the T7E1 Mutation Detection Assay.

Two cell lines, A549/Cas9 (GFP-Puro) cells and HEK293T cells, were used to evaluate the editing of EGFP and EMX1 genes. The sgRNA targeting EGFP and the sgRNA targeting EMX1 were synthesized (sequences in Table 1) and used for constructing corresponding LACM for editing EGFP and EMX1 in both cell lines.

A549/Cas9 (GFP-Puro) cells, with stable expression of Cas9 and GFP, were seeded in 96-well plate and treated with the LACM for 10 h. After irradiation with the 808-nm laser for 10 min, the cells were allowed to grow for 5 days. Cells were collected and genomic DNA extracted and analyzed using the T7E1 mutation assay.

HEK293T cells were cultured in Dulbecco's high glucose modified Eagle's medium (DMEM, Invitrogen) supplemented with 10% fetal bovine serum (FBS, Invitrogen) and 1% penicillin/streptomycin (pen/strep, Invitrogen). To produce intercellular Cas9, HEK 293T cells in 96-well plates were transfected with Cas9 plasmid DNA (LentiCRISPR v2 plasmid) using Lipofectamine 2000 reagent for 12 hours prior to treatment with LACM.

Rt-Qpcr.

Total RNA was extracted using a TRIzol reagent (#15596026, ThermoFisher Scientific). After removal of the growth medium, the TRIzol reagent was directly added to the plate for cell lysis and RNA extraction. The extracted RNA was precipitated and purified using isopropanol and 75% ethanol. Reverse transcription of extracted RNA was performed by using the iScript reverse transcription reagent kit, followed by real-time PCR amplification using the SYBR® Green Real-Time PCR master mix reagents kit with same qPCR primers as these used in the T7E1 assay.

Western Blotting Analysis.

The treated cells were washed twice with ice-cold PBS buffer, and lysed using ice-cold RIPA lysis buffer (150 mM NaCl, 1.0% Triton X-100, 0.5% sodium deoxycholate, 0.1% SDS, 50 mM Tris, pH 8.0, Sigma Aldrich). The cells were collected and transferred to a microfuge tube. Cell extract was agitated for 30 min at 4° C. and then centrifuged at 12,000 g for 15 min. The extracted protein in the supernatant was transferred to a new tube, and the protein concentration was quantified using the BCA protein assay kit (Sigma Aldrich). Approximately 10 µg of the total protein in 4× Laemmli loading buffer was heated at 98° C. for 10 min and loaded to a 12% SDS-PAGE gel for separation. After gel electrophoresis separation, the proteins were transferred onto a pre-washed polyvinylidene difluoride (PVDF) membrane. The membrane was then blocked for 1 h using 0.05% tween 20 and 5% BSA in 1×PBS buffer, followed by incubation with PLK-1 monoclonal antibody (#35-206, ThermoFisher Scientific) and monoclonal anti-β tubulin antibody (#T5201, Sigma) at 4° C. overnight. After removal of unbound antibodies by washing, the membrane was incubated with horse radish peroxidase (HRP)-labeled goat anti-mouse IgG (H+L) cross-adsorbed secondary antibody for 1 h at room temperature. The protein bands were then visualized by chemiluminescence detection. The band intensity was measured using the ImageJ software.

TABLE 1

Oligonucleotide sequences used in the study

| Oligonucleotides | Sequences (5'→3') | SEQ ID NO: |
|---|---|---|
| Protector-$T_{13}S_0$ | TGAAGTCGATGCC | 6 |
| Protector-$T_{14}S_0$ | TTGAAGTCGATGCC | 7 |
| Protector-$T_{15}S_0$ | CTTGAAGTCGATGCC | 8 |
| Protector-$T_{16}S_0$ | CCTTGAAGTCGATGCC | 9 |
| Protector-$T_{17}S_0$ | TCCTTGAAGTCGATGCC | 10 |
| Protector-$T_{18}S_0$ | CTCCTTGAAGTCGATGCC | 11 |
| Protector-$T_{16}S_6$ | CCTTGA AGTCGATGCC TCAAGG | 12 |
| Protector-$T_{16}S_7$ | CCTTGAAG TCGATGCC TTCAAG | 13 |
| Protector-$T_{16}S_8$ | CCTTGAAG TCGATGCC TTCAAGG | 14 |

TABLE 1-continued

Oligonucleotide sequences used in the study

| Oligonucleotides | Sequences (5'→3') | SEQ ID NO: |
|---|---|---|
| Protector-$T_{16}S_9$ | CCTTGAAGT CGATGCC ACTTCAAGG | 15 |
| Protector-$T_{16}S_0$ | CCTTGAAGTCGATGCC TTTTTTTTTT-SH | 16 |
| Protector for EGFP sgRNA | CCTTGAAG TCGATGCC TTCAAGG TTT-SH | 17 |
| sgRNA for EGFP | GGCAUCGACUUCAAGGAGGAGUUUUAGAGCUAGAAA UAGCAAGUUAAAAUAAGGCUAGUCCGUUAUCAACUU GAAAAAGUGGCACCGAGUCGGUGCUUUU | 18 |
| mutant sgRNA for EGFP | GGCAUCGACUUCAAGGAAAAGUUUUAGAGCUAGAAA UAGCAAGUUAAAAUAAGGCUAGUCCGUUAUCAACUU GAAAAAGUGGCACCGAGUCGGUGCUUUU | 19 |
| T7 promoter | TCTAATACGACTCACTATA | 20 |
| Forward primer for synthesizing sgRNA for EGFP | TCTAATACGACTCACTATAGGGCATCGACTTCAAGGAG GA GTTTTAGAGCTAGAAATAGCA | 21 |
| Forward primer for synthesizing mutant sgRNA for EGFP | TCTAATACGACTCACTATAGGGCATCGACTTCAAGGAAA A GTTTTAGAGCTAGAAATAGCA | 22 |
| Reverse primer for synthesizing sgRNA | AAAAGCACCGACTCGGTGCCACTTTTTCAAGTTGATAA CGGACTAGCCTTATTTTAACTTGCTATTTCTAGCTCTAAA AC | 23 |
| FAM-labeled DNA | FAM-AAAAGCACCGACTCGGTGCCACTTTTT | 24 |
| Forward primer for T7E1 assay for editing EGFP | GAGGAGCTGTTCACCGGG | 25 |
| Reverse primer for T7E1 assay for editing EGFP | CTTGTACAGCTCGTCCATGC | 26 |
| sgRNA for EMX1 | GAGUCCGAGCAGAAGAAGAAGUUUUAGAGCUAGAAA UAGCAAGUUAAAAUAAGGCUAGUCCGUUAUCAACUU GAAAAAGUGGCACCGAGUCGGUGCUUUU | 27 |
| mutant sgRNA for EMX1 | GAGUCCGAGCAGAAGAAUUAGUUUUAGAGCUAGAAA UAGCAAGUUAAAAUAAGGCUAGUCCGUUAUCAACUU GAAAAAGUGGCACCGAGUCGGUGCUUUU | 28 |
| Protector for EMX1 sgRNA | TCTTCTGC TCGGACTC GCAGAAGA TTT-SH | 29 |
| Forward primer for synthesizing sgRNA for EMX1 | TCTAATACGACTCACTATAGGAGTCCGAGCAGAAGAAG AA GTTTTAGAGCTAGAAATAGCA | 30 |
| Forward primer for synthesizing mutant sgRNA for EMX1 | TCTAATACGACTCACTATAGGAGTCCGAGCAGAAGAATT A GTTTTAGAGCTAGAAATAGCA | 31 |
| Forward primer for T7E1 assay for editing EMX1 | CTGTGTCCTCTTCCTGCCCT | 32 |
| Reverse primer for T7E1 assay for editing EMX1 | CTCTCCGAGGAGAAGGCCAA | 33 |
| sgRNA for PLK1 | UACCUACGGCAAAUUGUGCUGUUUUAGAGCUAGAAA UAGCAAGUUAAAAUAAGGCUAGUCCGUUAUCAACUU GAAAAAGUGGCACCGAGUCGGUGCUUUU | 34 |
| Mutant sgRNA for PLK1 | UACCUACGGCAAAUUGUUUUGUUUUAGAGCUAGAAA UAGCAAGUUAAAAUAAGGCUAGUCCGUUAUCAACUU GAAAAAGUGGCACCGAGUCGGUGCUUUU | 35 |

TABLE 1-continued

Oligonucleotide sequences used in the study

| Oligonucleotides | Sequences (5'→3') | SEQ ID NO: |
|---|---|---|
| Forward primer for synthesizing sgRNA for PLK1 | TAATACGACTCACTATAGGGTACCTACGGCAAATTGTGCT GTTTCAGAGCTATGCTGGA | 36 |
| Forward primer for synthesizing mutant sgRNA for PLK1 | TAATACGACTCACTATAGGGTACCTACGGCAAATTGTTTT GTTTCAGAGCTATGCTGGA | 37 |
| Protector for PLK1 sgRNA | CAATTTGC CGTAGGTA GCAAATTG TTT-SH | 38 |
| Forward primer for T7E1 assay for editing PLK1 | GGTGCTGCGAATGGTTGTGG | 39 |
| Reverse primer for T7E1 assay for editing PLK1 | CAGCCTCCTCCAAATTCCAGC | 40 |
| Scrambled RNA | GGCAUCGACUUCAAGGAGGAGUUUUAGAGCUAGAAA UAGCAAAUAAAAUAAAAAUAGUAUGUUUCCAAAGUGAA UAAUA CGUUGCUGGUGGCUGGUAUU | 41 |
| Reverse primer for synthesizing scrambled RNA | AATACCAGCCACCAGCAACGTATTATTCACTTTGGAAA CATACTATTTTTATTTTATTTTGCTATTTCTAGCTCTAAAAC | 42 |
| EMX1 On | GAGTCCGAGCAGAAGAAGAAGGG | 1 |
| EMX1 Off1 | GAGgCCGAGCAGAAGAAagACGG | 2 |
| EMX1 Off2 | GAGTCCtAGCAGgAGAAGAAGaG | 3 |
| EMX1 Off3 | GAGTCtaAGCAGAAGAAGAAGaG | 4 |
| EMX1 Off4 | GAGTtaGAGCAGAAGAAGAAAGG | 5 |
| Forward primer for Off1 | CAAAGGAGACCTGGAGACGAC | 43 |
| Reverse primer for Off1 | CCTAACAGGCACCCACATCA | 44 |
| Forward primer for Off2 | CACTGATTCATTAGGAGCTGGC | 45 |
| Reverse primer for Off2 | CTGGATTCTGCAGCAGCACAAC | 46 |
| Forward primer for Off3 | CACTAATACGGTTCTGTAAACGCC | 47 |
| Reverse primer for Off3 | CCTTACTATGTGCTGGGCACTG | 48 |
| Forward primer for Off4 | CCTGCAGACAGGAATAGCCCTAC | 49 |
| Reverse primer for Off4 | GCTTCTTATCCCTGTCTTCCAGG | 50 |
| TMR-Protector for EGFP sgRNA | TMR-TTCCTTGAAGTCGATGCCTTCAAGGTTT-SH | 52 |

REFERENCES (1) Cong, L.; Ran, F. A.; Cox, D.; Lin, S. L.; Barretto, R.; Habib, N.; Hsu, P. D.; Wu, X. B.; Jiang, W. Y.; Marraffini, L. A.; Zhang, F. Multiplex Genome Engineering Using CRISPR/Cas Systems. *Science* 2013, 339, 819-823.

(2) Doudna, J. A. Genomic Engineering and the Future of Medicine. *JAMA-J. Am. Med. Assoc.* 2015, 313, 791-792.

(3) Kirchner, M.; Schneider, S. CRISPR-Cas: From the Bacterial Adaptive Immune System to a Versatile Tool for Genome Engineering. *Angew. Chem. Int. Ed.* 2015, 54, 13508-13514.

(4) Swiech, L.; Heidenreich, M.; Banerjee, A.; Habib, N.; Li, Y. Q.; Trombetta, J.; Sur, M.; Zhang, F. In vivo Interrogation of Gene Function in the Mammalian Brain using CRISPR-Cas9. *Nat. Biotechnol.* 2015, 33, 102-106.

(5) Rouet, R.; Thuma, B. A.; Roy, M. D.; Lintner, N. G.; Rubitski, D. M.; Finley, J. E.; Wisniewska, H. M.; Mendonsa, R.; Hirsh, A.; de Onate, L. et al. Receptor-Mediated Delivery of CRISPR-Cas9 Endonuclease for Cell-Type-Specific Gene Editing. *J. Am. Chem. Soc.* 2018, 140, 6596-6603.

(6) Zuris, J. A.; Thompson, D. B.; Shu, Y.; Guilinger, J. P.; Bessen, J. L.; Hu, J. H.; Maeder, M. L.; Joung, J. K.; Chen, Z. Y.; Liu, D. R. Cationic Lipid-Mediated Delivery of Proteins Enables Efficient Protein-Based Genome Editing in vitro and in vivo. *Nat. Biotechnol.* 2015, 33, 73-80.

(7) Ryu, N.; Kim, M. A.; Park, D.; Lee, B.; Kim, Y. R.; Kim, K. H.; Baek, J. I.; Kim, W. J.; Lee, K. Y.; Kim, U. K. Effective PEI-Mediated Delivery of CRISPR-Cas9 Complex for Targeted Gene Therapy. *Nanomed-Nanotechnol.* 2018, 14, 2095-2102.

(8) Wang, P.; Zhang, L. M.; Zheng, W. F.; Cong, L. M.; Guo, Z. R.; Xie, Y. Z. Y.; Wang, L.; Tang, R. B.; Feng, Q.; Hamada, Y. et al. Thermo-Triggered Release of CRISPR-Cas9 System by Lipid-Encapsulated Gold Nanoparticles for Tumor Therapy. *Angew. Chem. Int. Ed.* 2018, 57, 1491-1496.

(9) Hansen-Bruhn, M.; de Avila, B. E. F.; Beltran-Gastelum, M.; Zhao, J.; Ramirez-Herrera, D. E.; Angsantikul, P.; Gothelf, K. V.; Zhang, L. F.; Wang, J. Active Intracellular Delivery of a Cas9/sgRNA Complex Using Ultrasound-Propelled Nanomotors. *Angew. Chem. Int. Ed.* 2018, 57, 2657-2661.

(10) Miller, J. B.; Zhang, S. Y.; Kos, P.; Xiong, H.; Zhou, K. J.; Perelman, S. S.; Zhu, H.; Siegwart, D. J. Non-Viral CRISPR/Cas Gene Editing in vitro and in vivo Enabled by Synthetic Nanoparticle Co-Delivery of Cas9 mRNA and sgRNA. *Angew. Chem. Int. Ed.* 2017, 56, 1059-1063.

(11) Pan, Y. C.; Yang, J. J.; Luan, X. W.; Liu, X. L.; Li, X. Q.; Yang, J.; Huang, T.; Sun, L.; Wang, Y. Z.; Lin, Y. H.; Song, Y. J. Near-Infrared Upconversion-Activated CRISPR-Cas9 System: A Remote-Controlled Gene Editing Platform. *Sci. Adv.* 2019, 5, eaav7199.

(12) Glass, Z.; Li, Y. M.; Xu, Q. B. Nanoparticles for CRISPR-Cas9 delivery. *Nat. Biomed. Eng.* 2017, 1, 854-855.

(13) Lee, B.; Lee, K.; Panda, S.; Gonzales-Rojas, R.; Chong, A.; Bugay, V.; Park, H. M.; Brenner, R.; Murthy, N.; Lee, H. Y. Nanoparticle Delivery of CRISPR into the Brain Rescues a Mouse Model of Fragile X Syndrome from Exaggerated Repetitive Behaviours. *Nat. Biomed. Eng.* 2018, 2, 497-507.

(14) Jain, P. K.; Ramanan, V.; Schepers, A. G.; Dalvie, N. S.; Panda, A.; Fleming, H. E.; Bhatia, S. N. Development of Light-Activated CRISPR Using Guide RNAs with Photocleavable Protectors. *Angew. Chem. Int. Ed.* 2016, 55, 12440-12444.

(15) Zhou, W. Y.; Deiters, A. Conditional Control of CRISPR/Cas9 Function. *Angew. Chem. Int. Ed.* 2016, 55, 5394-5399.

(16) Hemphill, J.; Borchardt, E. K.; Brown, K.; Asokan, A.; Deiters, A. Optical Control of CRISPR/Cas9 Gene Editing. *J. Am. Chem. Soc.* 2015, 137, 5642-5645.

(17) Nihongaki, Y.; Kawano, F.; Nakajima, T.; Sato, M. Photoactivatable CRISPR-Cas9 for Optogenetic Genome Editing. *Nat. Biotechnol.* 2015, 33, 755-760.

(18) Kong, J.; Wang, Y. F.; Zhang, J. X.; Qi, W.; Su, R. X.; He, Z. M. Rationally Designed Peptidyl Virus-Like Particles Enable Targeted Delivery of Genetic Cargo. *Angew. Chem. Int. Ed.* 2018, 57, 14032-14036.

(19) Hendel, A.; Bak, R. O.; Clark, J. T.; Kennedy, A. B.; Ryan, D. E.; Roy, S.; Steinfeld, I.; Lunstad, B. D.; Kaiser, R. J.; Wilkens, A. B. et al. Chemically Modified Guide RNAs Enhance CRISPR-Cas Genome Editing in Human Primary Cells. *Nat. Biotechnol.* 2015, 33, 985-989.

(20) Yin, H.; Kauffman, K. J.; Anderson, D. G. Delivery Technologies for Genome Editing. *Nat. Rev. Drug Discov.* 2017, 16, 387-399.

(21) Wilkinson, R. A.; Martin, C.; Nemudryi, A. A.; Wiedenheft, B. CRISPR RNA-Guided Autonomous Delivery of Cas9. *Nat. Struct. Mol. Biol.* 2019, 26, 14-24.

(22) Mout, R.; Ray, M.; Tonga, G. Y.; Lee, Y. W.; Tay, T.; Sasaki, K.; Rotello, V. M. Direct Cytosolic Delivery of CRISPR/Cas9-Ribonucleoprotein for Efficient Gene Editing. *ACS Nano* 2017, 11, 2452-2458.

(23) Luo, Y. L.; Xu, C. F.; Li, H. J.; Cao, Z. T.; Liu, J.; Wang, J. L.; Du, X. J.; Yang, X. Z.; Gu, Z.; Wang, J. Macrophage-Specific in vivo Gene Editing Using Cationic Lipid-Assisted Polymeric Nanoparticles. *ACS Nano* 2018, 12, 994-1005.

(24) Li, L.; Song, L. J.; Liu, X. W.; Yang, X.; Li, X.; He, T.; Wang, N.; Yang, S. L. X.; Yu, C.; Yin, T. et al. Artificial Virus Delivers CRISPR-Cas9 System for Genome Editing of Cells in Mice. *ACS Nano* 2017, 11, 95-111.

(25) Tang, W. X.; Hu, J. H.; Liu, D. R. Aptazyme-Embedded Guide RNAs Enable Ligand-Responsive Genome Editing and Transcriptional Activation. *Nat. Commun.* 2017, 8, 15939.

(26) Hirosawa, M.; Fujita, Y.; Parr, C. J. C.; Hayashi, K.; Kashida, S.; Hotta, A.; Woltjen, K.; Saito, H. Cell-Type-Specific Genome Editing with a microRNA-Responsive CRISPR-Cas9 Switch. *Nucleic Acids Res.* 2017, 45, 118.

(27) Yang, X. T.; Tang, Q.; Jiang, Y.; Zhang, M. N.; Wang, M.; Mao, L. Q. Nanoscale ATP-Responsive Zeolitic Imidazole Framework-90 as a General Platform for Cytosolic Protein Delivery and Genome Editing. *J. Am. Chem. Soc.* 2019, 141, 3782-3786.

(28) Chaverra-Rodriguez, D.; Macias, V. M.; Hughes, G. L.; Pujhari, S.; Suzuki, Y.; Peterson, D. R.; Kim, D.; McKeand, S.; Rasgon, J. L. Targeted Delivery of CRISPR-Cas9 Ribonucleoprotein into Arthropod Ovaries for Heritable Germline Gene Editing. *Nat. Commun.* 2018, 9, 3008.

(29) Kim, S. M.; Shin, S. C.; Kim, E. E.; Kim, S. H.; Park, K.; Oh, S. J.; Jang, M. Simple in vivo Gene Editing via Direct Self-Assembly of Cas9 Ribonucleoprotein Complexes for Cancer Treatment. *ACS Nano* 2018, 12, 7750-7760.

(30) Wang, J.; Wei, Y. R.; Hu, X. X.; Fang, Y. Y.; Li, X. Y.; Liu, J.; Wang, S. F.; Yuan, Q. Protein Activity Regulation: Inhibition by Closed-Loop Aptamer-Based Structures and Restoration by Near-IR Stimulation. *J. Am. Chem. Soc.* 2015, 137, 10576-10584.

(31) Du, Y.; Jiang, Q.; Beziere, N.; Song, L. L.; Zhang, Q.; Peng, D.; Chi, C. W.; Yang, X.; Guo, H. B.; Diot, G. et al. DNA-Nanostructure-Gold-Nanorod Hybrids for Enhanced in vivo Optoacoustic Imaging and Photothermal Therapy. *Adv. Mater.* 2016, 28, 10000-10007.

(32) Wang, W. J.; Satyavolu, N. S. R.; Wu, Z. K.; Zhang, J. R.; Zhu, J. J.; Lu, Y. Near-Infrared Photothermally Activated DNAzyme-Gold Nanoshells for Imaging Metal Ions in Living Cells. *Angew. Chem. Int. Ed.* 2017, 56, 6798-6802.

(33) Qiu, M.; Wang, D.; Liang, W. Y.; Liu, L. P.; Zhang, Y.; Chen, X.; Sang, D. K.; Xing, C. Y.; Li, Z. J.; Dong, B. Q. et al. Novel Concept of the Smart NIR-Light-Controlled Drug Release of Black Phosphorus Nanostructure for Cancer Therapy. *Proc. Natl. Acad. Sci. U.S.A.* 2018, 115, 501-506.

(34) Cutler, J. I.; Auyeung, E.; Mirkin, C. A., Spherical Nucleic Acids. J. Am. Chem. Soc. 2012, 134, 1376-1391.
(35) Qing, Z. H.; Xu, J. Y.; Hu, J. L.; Zheng, J.; He, L.; Zou, Z.; Yang, S.; Tan, W. H.; Yang, R. H., In Situ Amplification Based Imaging of RNA in Living Cells. Angew. Chem. Int. Ed. 2019, 58, 11574-11585
(36) Choi, C. H. J.; Hao, L. L.; Narayan, S. P.; Auyeung, E.; Mirkin, C. A., Mechanism for the Endocytosis of Spherical Nucleic Acid Nanoparticle Conjugates. Proc. Natl. Acad. Sci. U.S.A. 2013, 110, 7625-7630.
(37) Li, H.; Zhang, B. H.; Lu, X. G.; Tan, X. Y.; Jia, F.; Xiao, Y.; Cheng, Z. H.; Li, Y.; Silva, D. O.; Schrekker, H. S.; Zhang, K.; Mirkin, C. A., Molecular Spherical Nucleic Acids. Proc. Natl. Acad. Sci. U.S.A. 2018, 115, 4340-4344.
(38) Giljohann, D. A.; Seferos, D. S.; Prigodich, A. E.; Patel, P. C.; Mirkin, C. A., Gene Regulation with Polyvalent siRNA-Nanoparticle Conjugates. J. Am. Chem. Soc. 2009, 131, 2072-2073.
(39) Davis, K. M.; Pattanayak, V.; Thompson, D. B.; Zuris, J. A.; Liu, D. R., Small Molecule-triggered Cas9 Protein with Improved Genome-editing Specificity. Nat. Chem. Biol. 2015, 11, 316-318.
(40) Fu, Y. F.; Foden, J. A.; Khayter, C.; Maeder, M. L.; Reyon, D.; Joung, J. K.; Sander, J. D., High-frequency Off-target Mutagenesis Induced by CRISPR-Cas Nucleases in Human Cells. Nat. Biotechnol. 2013, 31, 822-826.
(41) Fu, Y. F.; Sander, J. D.; Reyon, D.; Cascio, V. M.; Joung, J. K., Improving CRISPR-Cas Nuclease Specificity Using Truncated Guide RNAs. Nat. Biotechnol. 2014, 32, 279-284.
(42) Ran, F. A.; Hsu, P. D.; Lin, C. Y.; Gootenberg, J. S.; Konermann, S.; Trevino, A. E.; Scott, D. A.; Inoue, A.; Matoba, S.; Zhang, Y.; Zhang, F., Double Nicking by RNA-Guided CRISPR Cas9 for Enhanced Genome Editing Specificity. Cell 2013, 154, 1380-1389.
(43) Spankuch-Schmitt, B.; Bereiter-Hahn, A.; Kaufmann, M.; Strebhardt, K., Effect of RNA Silencing of Polo-like Kinase-1 (PLK1) on Apoptosis and Spindle Formation in Human Cancer Cells. J. Natl. Cancer I 2002, 94, 1863-1877.
(44) Wang, P.; Zhang, L. M.; Xie, Y. Z. Y.; Wang, N. X.; Tang, R. B.; Zheng, W. F.; Jiang, X. Y., Genome Editing for Cancer Therapy: Delivery of Cas9 Protein/sgRNA Plasmid via a Gold Nanocluster/Lipid Core-Shell Nanocarrier. Adv. Sci. 2017, 4, 1700175.
(45) Lei, Y. F.; Tang, L. X.; Xie, Y. Z. Y.; Xianyu, Y. L.; Zhang, L. M.; Wang, P.; Hamada, Y.; Jiang, K.; Zheng, W. F.; Jiang, X. Y., Gold Nanoclusters-assisted Delivery of NGF siRNA for Effective Treatment of Pancreatic Cancer. Nat. Commun. 2017, 8, 15130.
(46) Zhang, X.; Huang, P. J. J.; Servos, M. R.; Liu, J. W., Effects of Polyethylene Glycol on DNA Adsorption and Hybridization on Gold Nanoparticles and Graphene Oxide. Langmuir 2012, 28, 14330-14337.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The invention claimed is:

1. An isolated protector polynucleotide for reversible binding to an sgRNA, consisting of or comprising the structure of Formula (I),

T-S-L                    (I)

wherein,

T comprises a targeting sequencing domain polynucleotide that reversibly hybridizes to a target binding domain of an sgRNA;

S comprises a stem domain polynucleotide sequence that forms a hairpin structure when said protector polynucleotide is not bound to said sgRNA; and L comprises a linker polynucleotide sequence having a first end attached to said S, and a second end for attachment to a nanostructure, wherein the protector polynucleotide and the sgRNA are separate nucleic acid molecules and wherein said T is displaceable from said sgRNA upon exposure of the isolated protector polynucleotide to a low-power NIR laser.

2. The isolated polynucleotide of claim 1, wherein said T is 13, 14, 15, 16, 17, or 18 nucleotides in length.

3. The isolated polynucleotide of claim 1, wherein said S is 6, 7, 8, or 9 nucleotides in length.

4. The isolated polynucleotide of claim 1, wherein L comprises a thiol moiety positioned at the 3' end.

5. The isolated protector polynucleotide of claim 1, wherein said linker polynucleotide sequence is about three nucleotides long.

6. A kit comprising the isolated protector polynucleotide for reversible binding to an sgRNA according to claim 1, a container, and optionally instructions for the use thereof.

7. An isolated system, comprising:

an sgRNA;

a protector polynucleotide consisting of or comprising the structure of Formula (I),

T-S-L                    (I)

wherein:

T comprises a targeting sequencing domain polynucleotide bound to a target binding domain of said sgRNA;

S comprises a stem domain polynucleotide sequence that forms a hairpin structure when said protector polynucleotide is not bound to said sgRNA; and L comprises a linker polynucleotide sequence having a first end attached to said S, and a second end for removable attachment to a support; and the support attached to said second end of said L, wherein the protector polynucleotide and the sgRNA are separate nucleic acid molecules and said T is displaceable from said sgRNA upon exposure of the protector polynucleotide to a low-power NIR laser.

8. The system of claim 7, wherein said T is 13, 14, 15, 16, 17, or 18 nucleotides in length.

9. The system of claim 7, wherein said S is 6, 7, 8, or 9 nucleotides in length.

10. The system of claim 7, wherein said support comprises a nanostructure.

11. The system of claim 10, wherein said support comprises a noble metal.

12. The system of claim 11, wherein said noble metal comprises a nanoparticle.

13. The system of claim 11, wherein said noble metal is gold.

14. The system of claim 10, wherein said support is a gold nanorod (AuNR).

15. The isolated system of claim 7, wherein said linker polynucleotide sequence is about three nucleotides long.

16. A kit comprising the isolated system according to claim 7, a container, and optionally instructions for the use thereof.

* * * * *